US008741293B2

(12) United States Patent
Dodel et al.

(10) Patent No.: US 8,741,293 B2
(45) Date of Patent: Jun. 3, 2014

(54) NATURALLY OCCURRING AUTOANTIBODIES AGAINST ALPHA-SYNUCLEIN THAT INHIBIT THE AGGREGATION AND CYTOTOXICITY OF ALPHA-SYNUCLEIN

(75) Inventors: Richard Dodel, Niederweimar an der Lahn (DE); Michael Bacher, Marburg (DE); Daniela Besong Agbo, Marburg (DE); Sascha Hagemann, Marburg (DE); Monika Balzer-Geldsetzer, Ismaning (DE); Bernd Rehberger, Laupheim (DE); Renee Weber, Laupheim (DE)

(73) Assignee: Dr. Rentschler Holding GmbH & Co. KG, Laupheim (DE)

( * ) Notice: Subject to any disclaimer, the term of this patent is extended or adjusted under 35 U.S.C. 154(b) by 0 days.

(21) Appl. No.: 13/582,489

(22) PCT Filed: Mar. 3, 2011

(86) PCT No.: PCT/EP2011/053188
§ 371 (c)(1), (2), (4) Date: Nov. 12, 2012

(87) PCT Pub. No.: WO2011/107544
PCT Pub. Date: Sep. 9, 2011

(65) Prior Publication Data

US 2013/0052200 A1 Feb. 28, 2013

(30) Foreign Application Priority Data

Mar. 3, 2010 (EP) .................................... 10155373

(51) Int. Cl.
*C07K 16/18* (2006.01)
*A61K 39/395* (2006.01)
*A61K 39/00* (2006.01)
*C12P 21/00* (2006.01)

(52) U.S. Cl.
USPC .... 424/139.1; 435/69.6; 435/331; 530/387.9; 536/23.53

(58) Field of Classification Search
CPC combination set(s) only.
See application file for complete search history.

(56) References Cited

U.S. PATENT DOCUMENTS

2009/0208487 A1 * 8/2009 Schenk et al. ............ 424/133.1

FOREIGN PATENT DOCUMENTS

WO 2009133521 A2 11/2009

OTHER PUBLICATIONS

Southwell et al., Antibody therapy in Neurodegenerative Disease. Reviews in the Neurosciences 21, 273-287 (2010).*
Neff F et al: "Immunotherapy and naturally occurring autoantibodies in neurodegenerative disorders" Autoimmunity Reviews, vol. 7, No. 6, Jun. 1, 2008, pp. 501-507.
Emadi et al: "Isolation of a Human Single Chain Antibody Fragment Against Oligomeric alpha-Synuclein that Inhibits Aggregation and Prevents alpha-Synuclein-induced Toxicity" Journal of Molecular Biology, vol. 368, No. 4, Apr. 17, 2007, pp. 1132-1144.
Papachroni Katerina K et al: "Autoantibodies to alpha-synuclein in inherited Parkinson's disease" Journal of Neurochemistry vol. 101, No. 3, May 1, 2007, pp. 749-756.
Masliah E et al: "Effects of alpha-synuclein immunization in a mouse model of Parkinson's disease" Neuron, Cell Press, vol. 46, No. 6, Jun. 16, 2005, pp. 857-868.

* cited by examiner

*Primary Examiner* — Jeffrey Stucker
*Assistant Examiner* — Aurora M Fontainhas
(74) *Attorney, Agent, or Firm* — Rothwell, Figg, Ernst & Manbeck, P.C.

(57) ABSTRACT

The present invention refers to human antibodies which are directed against α-Synuclein (α-Syn) and their use in medicine and diagnosis.

Figure 1:
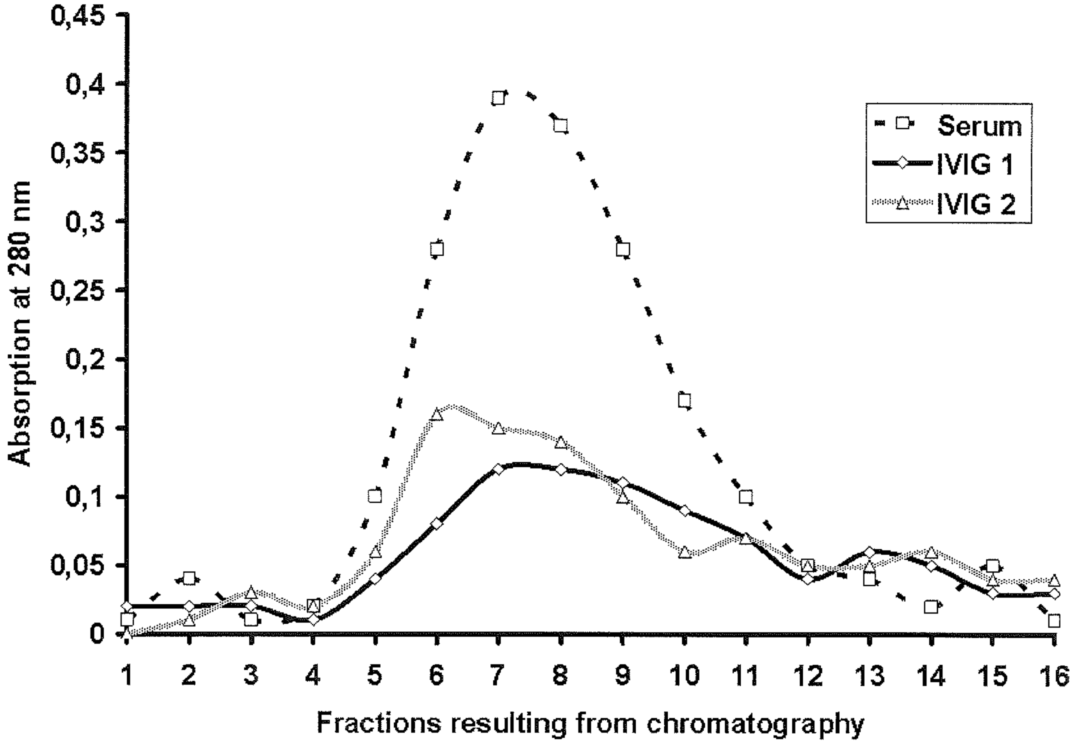

4 Claims, 15 Drawing Sheets anti-α-Synuclein $HC_v$ Type 1:

| | | | | | | |
|---|---|---|---|---|---|---|
| QVQLVESGGGVVQPGRSLRLSCAAS | **CDR1** | WVRQAPGKGLEWVA | **CDR2** | RFTISRDNSKNTLYLQMNSLRAEDTAVYYCAR | **CDR3** | (continued below) |
| 1 amino acid position 25 | | 26 amino acid pos. 39 | | 40 amino acid position 71 | | |

| | | |
|---|---|---|
| (continued from above) | **CDR3** | WGQGTTVTVSSASTKGPSVFPLAPSSKSTSGGTAALGCLVKDYFPEPVTV |
| | | 72 amino acid position 121 |

Possible amino acid exchanges within anti-αSynuclein $HC_v$ Type 1 antibodies:

| Pos. | Consensus | Variants |
|---|---|---|
| 1 | Q | E / G |
| 5 | V | L |
| 10 | G | D |
| 11 | V | L |
| 13 | Q | K |
| 16 | R | G |
| 19 | R | G |
| 23 | A | V |

| Pos. | Con. | Var. |
|---|---|---|
| 26 | W | R |
| 27 | V | I |
| 39 | A | G/S |

| Pos. | Consensus | Variants |
|---|---|---|
| 47 | N | D |
| 61 | A | T |
| 48 | S | A |
| 51 | T | S |

| Pos. | Consensus | Variants |
|---|---|---|
| 72 | W | V |
| 74 | Q | K |
| 75 | G | E |
| 77 | T | L / M |
| 79 | T | N |
| 96 | S | C |
| 98 | K | R |
| 102 | G | E |
| 103 | G | S |

(Linked amino acid exchanges depicted within one box)

Figure 2
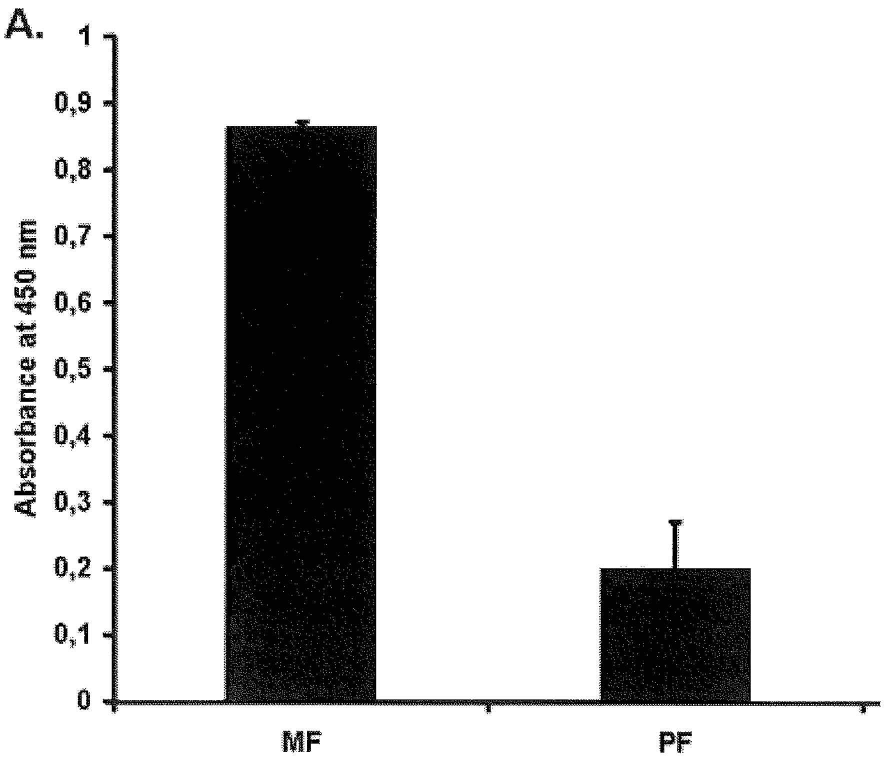
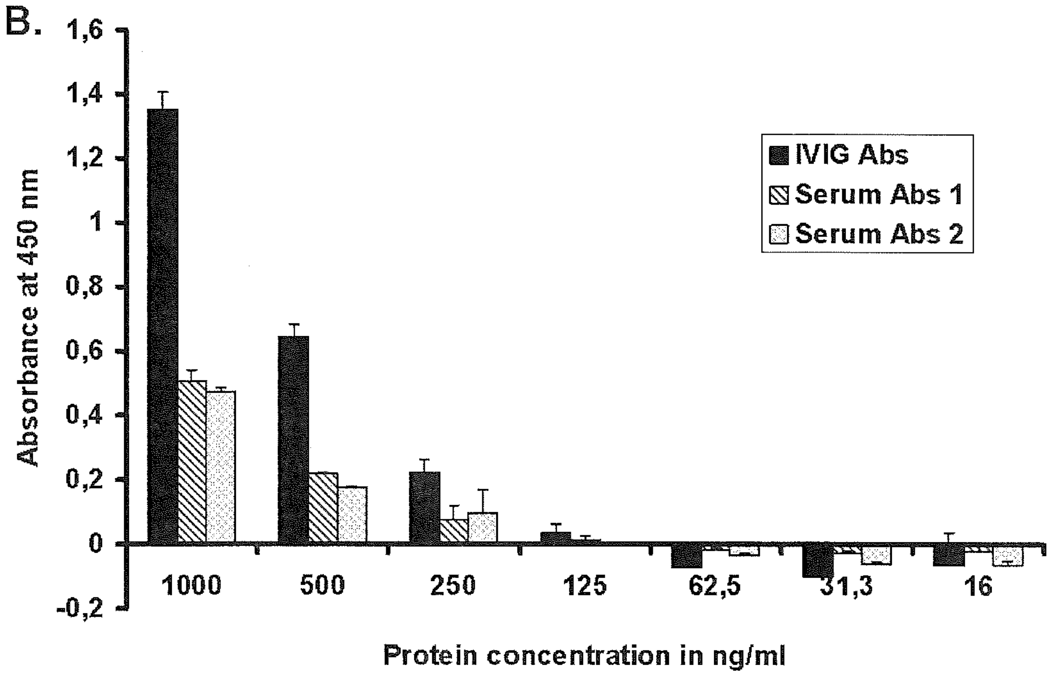

Figure 5
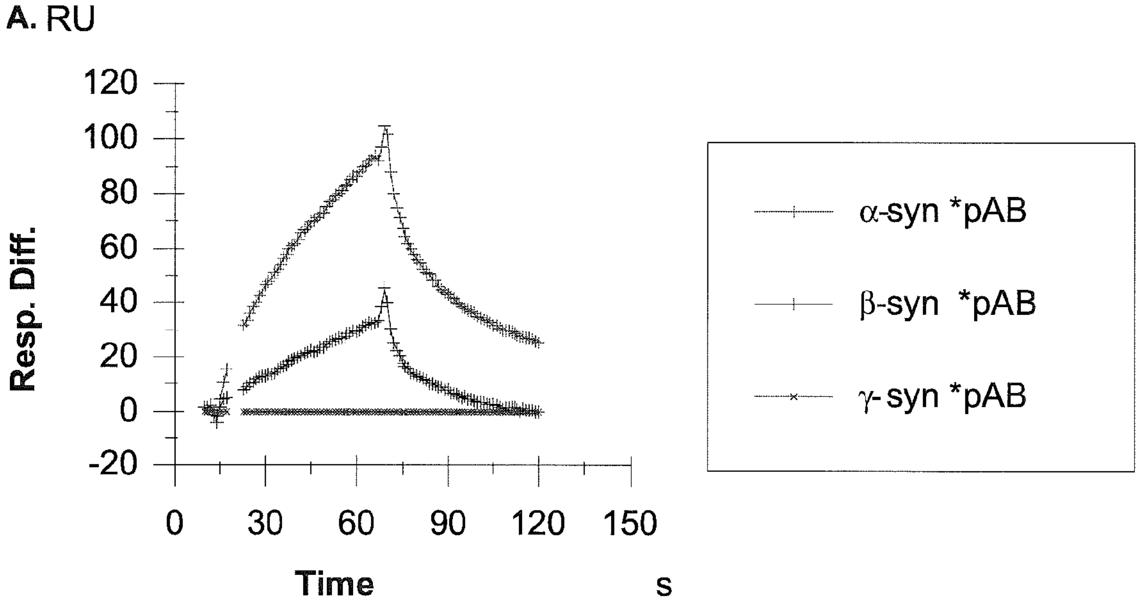
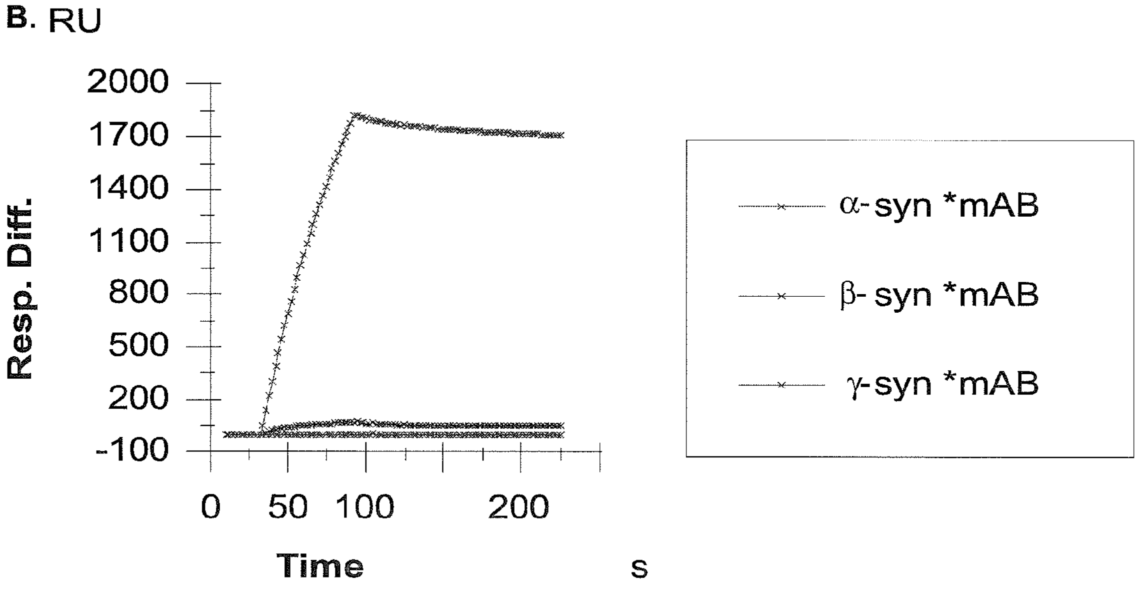

Figure 8 anti-α-Synuclein $HC_v$ Type 1:

| | | | | | | |
|---|---|---|---|---|---|---|
| QVQLVESGGGVVQPGRSLRLSCAAS | CDR1 | WVRQAPGKGLEWVA | CDR2 | RFTISRDNSKNTLYLQMNSLRAEDTAVYYCAR | CDR3 | (continued below) |
| 1 amino acid position 25 | | 26 amino acid pos. 39 | | 40 amino acid position 71 | | |

| | | |
|---|---|---|
| (continued from above) | CDR3 | WGQGTTVTVSSASTKGPSVFPLAPSSKSTSGGTAALGCLVKDYFPEPVTV |
| | | 72 amino acid position 121 |

Possible amino acid exchanges within anti-αSynuclein $HC_v$ Type 1 antibodies:

| Pos. | Consensus | Variants |
|---|---|---|
| 1 | Q | E / G |
| 5 | V | L |
| 10 | G | D |
| 11 | V | L |
| 13 | Q | K |
| 16 | R | G |
| 19 | R | G |
| 23 | A | V |

| Pos. | Con. | Var. |
|---|---|---|
| 26 | W | R |
| 27 | V | I |
| 39 | A | G/S |

| Pos. | Consensus | Variants |
|---|---|---|
| 47 | N | D |
| 61 | A | T |
| 48 | S | A |
| 51 | T | S |

| Pos. | Consensus | Variants |
|---|---|---|
| 72 | W | V |
| 74 | Q | K |
| 75 | G | E |
| 77 | T | L / M |
| 79 | T | N |
| 96 | S | C |
| 98 | K | R |
| 102 | G | E |
| 103 | G | S |

(Linked amino acid exchanges depicted within one box)

Figure 9 anti-α-Synuclein $HC_v$ Type 2:

| QLQLQESGSGLVKPSQTLSLTCAVS | CDR1 | WIRQPPGKGLEWIG | CDR2 | RVTISVDRSKNQFSLKLSSVTAADTAVYYCAR | CDR3 | (continued below) |
|---|---|---|---|---|---|---|
| 1 amino acid position 25 | | 26 amino acid pos. 39 | | 40 amino acid position 71 | | |

| (continued from above) | CDR3 | WGKGTTVTVSSASTKGPSVFPLAPSSKSTSGGTAALGCLVKDYFPEPVTV |
|---|---|---|
| | | 72 amino acid position 121 |

Possible amino acid exchanges within Anti-αSynuclein $HC_v$ Type 2 antibodies:

| Pos. | Consensus | Variants |
|---|---|---|
| 2 | L | V |
| 9 | S | P |
| 23 | A | T |

| Pos. | Con. | Var. |
|---|---|---|
| 31 | P | H |

| Pos. | Consensus | Variants |
|---|---|---|
| 47 | R | T |
| 55 | K | R |

| Pos. | Consensus | Variants |
|---|---|---|
| 74 | K | Q |
| 77 | T | L |
| 96 | S | C |

(Linked amino acid exchanges depicted within one box)

Figure 10 anti-α-Synuclein $HC_v$ Type 3:

| QVQLVQSGAEVKKPGASVKVSCKAS | CDR1 | WVRQAPGQGLEWMG | CDR2 | WVTMTRDTSISTAYMELSRLRSDDTAVYYCAR | CDR3 | (continued below) |
|---|---|---|---|---|---|---|
| 1 amino acid position 25 | | 26 amino acid pos. 39 | | 40 amino acid position 71 | | |

| (continued from above) | CDR3 | WGRGTLVTVSSASTKGPSVFPLAPCSRSTSESTAALGCLVKDYFPEPVTV |
|---|---|---|
| | | 72 amino acid position 121 |

Possible amino acid exchanges within Anti-αSynuclein $HC_v$ Type 3 antibodies:

| Pos. | Consensus | Variants |
|---|---|---|
| 16 | A | S |

| Pos. | Con. | Var. |
|---|---|---|
| n/a | n/a | n/a |

| Pos. | Consensus | Variants |
|---|---|---|
| 40 | W | R |
| 43 | M | I |
| 45<br>47<br>49<br>58<br>62 | R<br>T<br>I<br>R<br>D | A<br>E<br>T<br>S<br>E |
| 45<br>49<br>52<br>55<br>58<br>62 | R<br>I<br>A<br>E<br>R<br>D | S<br>T<br>V<br>H<br>S<br>E |
| 71 | R | T |

| Pos. | Consensus | Variants |
|---|---|---|
| 74 | R | P / K / Q |
| 77 | L | T |
| 96 | C | S |
| 98 | R | K |
| 100 | T | A |
| 102<br>103 | E<br>S | G<br>G |
| 119<br>120 | V<br>T | G<br>R |
| 121 | V | G |

(Linked amino acid exchanges depicted within one box)

Figure 11 anti-α-Synuclein $LC_v$ Type 1:

| DIVMTQSPLSLPVTPGEPASISC | CDR1 | WYLQKPGQSPQLLIY | CDR2 | GVPDRFSGSGSGTDFTLKISRVEAEDVGVYYC | CDR3 | (continued below) |
|---|---|---|---|---|---|---|
| 1 amino acid position 23 | | 24 amino acid pos. 38 | | 39 amino acid position 70 | | |

| (continued from above) | CDR3 | FGQGTKLEIKRTVAAP |
|---|---|---|
| | | 71 amino acid position 86 |

Possible amino acid exchanges within Anti-αSynuclein $LC_v$ Type 1 antibodies:

| Pos. | Consensus | Variants |
|---|---|---|
| 7 | S | T |

| Pos. | Con. | Var. |
|---|---|---|
| n/a | n/a | n/a |

| Pos. | Con. | Variants |
|---|---|---|
| 57 | S | G |

| Pos. | Con. | Var. |
|---|---|---|
| 76 | K | R |
| 77 | L | V |
| 79 | I | S |
| 84 | A | T |

Figure 12 anti-α-Synuclein $LC_v$ Type 2:

| | | | | | | |
|---|---|---|---|---|---|---|
| EIVLTQSPGTLSLSPGERATLSC | CDR1 | WYQQKPGQAPRLLIY | CDR2 | GIPDRFSGSGSGTDFTLTISRLEPEDFAVYYC | CDR3 | (continued below) |
| 1 amino acid position 23 | | 24 amino acid pos. 38 | | 39 amino acid position 70 | | |

| | | |
|---|---|---|
| (continued from above) | CDR3 | FGQGTKVEIKRTVAAP |
| | | 71 amino acid pos. 86 |

Possible amino acid exchanges within Anti-αSynuclein $LC_v$ Type 2 antibodies:

| Pos. | Consensus | Variants |
|---|---|---|
| 1 | E | K |
| 4<br>13 | L<br>L | M<br>V |
| 9 | G | A |
| 22 | S | P |

| Pos. | Con. | Var. |
|---|---|---|
| n/a | n/a | n/a |

| Pos. | Con. | Variants |
|---|---|---|
| 42 | D | A |
| 52 | D | E |
| 56 | T | I |
| 59 | R | S |
| 61<br>62 | E<br>P | Q<br>S |
| 63 | E | K |

| Pos. | Con. | Var. |
|---|---|---|
| 73 | Q | G |
| 76<br>77 | K<br>V | R<br>L |

(Linked amino acid exchanges depicted within one box)

Figure 13 anti-α-Synuclein $LC_v$ Type 3:

| DIQMTQSPSSLSASVGDRVTITC | CDR1 | WFQQKPGKAPKSLIY | CDR2 | GVPSKFSGSGSGTDFTLTISSLQPEDFATYYC | CDR3 | (continued below) |
|---|---|---|---|---|---|---|
| 1 amino acid position 23 | | 24 amino acid pos. 38 | | 39 amino acid position 70 | | |

| (continued from above) | CDR3 | FGQGTKLEIKRTVAAP |
|---|---|---|
| | | 71 amino acid pos. 86 |

Possible amino acid exchanges within anti-αSynuclein $LC_v$ Type 3 antibodies:

| Pos. | Consensus | Variants |
|---|---|---|
| 1 | D | A / V |
| 3 | Q | W |
| 5 | T | A |
| 10 | S | T / L |
| 11 | L | V |
| 22 | T | S |

| Pos. | Con. | Var. |
|---|---|---|
| 25 | F | Y |
| 28 | K | R |
| 30 | G | R |
| 35 | S | L / R |

| Pos. | Con. | Variants |
|---|---|---|
| 43 | K | R |
| 52 | D | E |
| 55 | L | F |
| 58 | S | T |
| 59 | S | T |
| 63 | E | D |
| 65 | F | I / S |
| 67 | T | N |

| Pos. | Con. | Var. |
|---|---|---|
| 73 | Q | P |
| 77 | L | V |
| 78 | E | D |

(Linked amino acid exchanges depicted within one box)

SEQUENCE LISTING

```
<160> NUMBER OF SEQ ID NOS: 164

<210> SEQ ID NO 1
<211> LENGTH: 140
```

```
<212> TYPE: PRT
<213> ORGANISM: Homo sapiens
<220> FEATURE:
<221> NAME/KEY: MISC_FEATURE
<222> LOCATION: (1)..(140)
<223> OTHER INFORMATION: alpha-Synuclein

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140


<210> SEQ ID NO 2
<211> LENGTH: 220
<212> TYPE: PRT
<213> ORGANISM: Homo sapiens
<220> FEATURE:
<221> NAME/KEY: MISC_FEATURE
<222> LOCATION: (1)..(220)
<223> OTHER INFORMATION: light chain sequence

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Ser Glu Asp Phe Ala Thr Tyr Tyr Cys Arg Leu Thr Glu Glu Lys Gly
                85                  90                  95

Trp Met Tyr Leu Gly Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 3
<211> LENGTH: 25
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser
            20                  25


<210> SEQ ID NO 4
<211> LENGTH: 14
<212> TYPE: PRT
<213> ORGANISM: Homo sapiens

<400> SEQUENCE: 4

Trp Val Arg Gln Ala Pro Gly Lys Gly Leu Glu Trp Val Ala
1               5                   10


<210> SEQ ID NO 5
<211> LENGTH: 32
<212> TYPE: PRT
<213> ORGANISM: Homo sapiens

<400> SEQUENCE: 5

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30


<210> SEQ ID NO 6
<211> LENGTH: 50
<212> TYPE: PRT
<213> ORGANISM: Homo sapiens

<400> SEQUENCE: 6

Trp Gly Gln Gly Thr Thr Val Thr Val Ser Ser Ala Ser Thr Lys Gly
1               5                   10                  15

Pro Ser Val Phe Pro Leu Ala Pro Ser Ser Lys Ser Thr Ser Gly Gly
            20                  25                  30

Thr Ala Ala Leu Gly Cys Leu Val Lys Asp Tyr Phe Pro Glu Pro Val
        35                  40                  45

Thr Val
    50


<210> SEQ ID NO 7
<211> LENGTH: 25
<212> TYPE: PRT
<213> ORGANISM: Homo sapiens

<400> SEQUENCE: 7

Gln Leu Gln Leu Gln Glu Ser Gly Ser Gly Leu Val Lys Pro Ser Gln
1               5                   10                  15
```

Thr Leu Ser Leu Thr Cys Ala Val Ser
20 25

<210> SEQ ID NO 8
<211> LENGTH: 14
<212> TYPE: PRT
<213> ORGANISM: Homo sapiens

<400> SEQUENCE: 8

Trp Ile Arg Gln Pro Pro Gly Lys Gly Leu Glu Trp Ile Gly
1 5 10

<210> SEQ ID NO 9
<211> LENGTH: 32
<212> TYPE: PRT
<213> ORGANISM: Homo sapiens

<400> SEQUENCE: 9

Arg Val Thr Ile Ser Val Asp Arg Ser Lys Asn Gln Phe Ser Leu Lys
1 5 10 15

Leu Ser Ser Val Thr Ala Ala Asp Thr Ala Val Tyr Tyr Cys Ala Arg
20 25 30

<210> SEQ ID NO 10
<211> LENGTH: 50
<212> TYPE: PRT
<213> ORGANISM: Homo sapiens

<400> SEQUENCE: 10

Trp Gly Lys Gly Thr Thr Val Thr Val Ser Ser Ala Ser Thr Lys Gly
1 5 10 15

Pro Ser Val Phe Pro Leu Ala Pro Ser Ser Lys Ser Thr Ser Gly Gly
20 25 30

Thr Ala Ala Leu Gly Cys Leu Val Lys Asp Tyr Phe Pro Glu Pro Val
35 40 45

Thr Val
50

<210> SEQ ID NO 11
<211> LENGTH: 25
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 12
<211> LENGTH: 14
<212> TYPE: PRT
<213> ORGANISM: Homo sapiens

<400> SEQUENCE: 12

Trp Val Arg Gln Ala Pro Gly Gln Gly Leu Glu Trp Met Gly
1 5 10

<210> SEQ ID NO 13
<211> LENGTH: 32
<212> TYPE: PRT
<213> ORGANISM: Homo sapiens

<400> SEQUENCE: 13

-continued

```
Trp Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30


<210> SEQ ID NO 14
<211> LENGTH: 50
<212> TYPE: PRT
<213> ORGANISM: Homo sapiens

<400> SEQUENCE: 14

Trp Gly Arg Gly Thr Leu Val Thr Val Ser Ser Ala Ser Thr Lys Gly
1               5                   10                  15

Pro Ser Val Phe Pro Leu Ala Pro Cys Ser Arg Ser Thr Ser Glu Ser
            20                  25                  30

Thr Ala Ala Leu Gly Cys Leu Val Lys Asp Tyr Phe Pro Glu Pro Val
        35                  40                  45

Thr Val
    50


<210> SEQ ID NO 15
<211> LENGTH: 23
<212> TYPE: PRT
<213> ORGANISM: Homo sapiens

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys
            20


<210> SEQ ID NO 16
<211> LENGTH: 15
<212> TYPE: PRT
<213> ORGANISM: Homo sapiens

<400> SEQUENCE: 16

Trp Tyr Leu Gln Lys Pro Gly Gln Ser Pro Gln Leu Leu Ile Tyr
1               5                   10                  15


<210> SEQ ID NO 17
<211> LENGTH: 32
<212> TYPE: PRT
<213> ORGANISM: Homo sapiens

<400> SEQUENCE: 17

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30


<210> SEQ ID NO 18
<211> LENGTH: 16
<212> TYPE: PRT
<213> ORGANISM: Homo sapiens

<400> SEQUENCE: 18

Phe Gly Gln Gly Thr Lys Leu Glu Ile Lys Arg Thr Val Ala Ala Pro
1               5                   10                  15


<210> SEQ ID NO 19
<211> LENGTH: 23
```

<212> TYPE: PRT
<213> ORGANISM: Homo sapiens

<400> SEQUENCE: 19

```
Glu Ile Val Leu Thr Gln Ser Pro Gly Thr Leu Ser Leu Ser Pro Gly
1               5                   10                  15

Glu Arg Ala Thr Leu Ser Cys
            20
```

<210> SEQ ID NO 20
<211> LENGTH: 15
<212> TYPE: PRT
<213> ORGANISM: Homo sapiens

<400> SEQUENCE: 20

```
Trp Tyr Gln Gln Lys Pro Gly Gln Ala Pro Arg Leu Leu Ile Tyr
1               5                   10                  15
```

<210> SEQ ID NO 21
<211> LENGTH: 32
<212> TYPE: PRT
<213> ORGANISM: Homo sapiens

<400> SEQUENCE: 21

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30
```

<210> SEQ ID NO 22
<211> LENGTH: 16
<212> TYPE: PRT
<213> ORGANISM: Homo sapiens

<400> SEQUENCE: 22

```
Phe Gly Gln Gly Thr Lys Val Glu Ile Lys Arg Thr Val Ala Ala Pro
1               5                   10                  15
```

<210> SEQ ID NO 23
<211> LENGTH: 23
<212> TYPE: PRT
<213> ORGANISM: Homo sapiens

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 24
<211> LENGTH: 15
<212> TYPE: PRT
<213> ORGANISM: Homo sapiens

<400> SEQUENCE: 24

```
Trp Phe Gln Gln Lys Pro Gly Lys Ala Pro Lys Ser Leu Ile Tyr
1               5                   10                  15
```

<210> SEQ ID NO 25
<211> LENGTH: 32
<212> TYPE: PRT
<213> ORGANISM: Homo sapiens

<400> SEQUENCE: 25

Gly Val Pro Ser Lys Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 26
<211> LENGTH: 16
<212> TYPE: PRT
<213> ORGANISM: Homo sapiens

<400> SEQUENCE: 26

Phe Gly Gln Gly Thr Lys Leu Glu Ile Lys Arg Thr Val Ala Ala Pro
1 5 10 15

<210> SEQ ID NO 27
<211> LENGTH: 10
<212> TYPE: PRT
<213> ORGANISM: Artificial
<220> FEATURE:
<223> OTHER INFORMATION: anti-alpha-Synuclein HCv Type 1, CDR1, consensus sequence
<220> FEATURE:
<221> NAME/KEY: MISC_FEATURE
<222> LOCATION: (4)..(4)
<223> OTHER INFORMATION: Xaa may be Phe or Val
<220> FEATURE:
<221> NAME/KEY: MISC_FEATURE
<222> LOCATION: (6)..(6)
<223> OTHER INFORMATION: Xaa may be Asp or Ser
<220> FEATURE:
<221> NAME/KEY: MISC_FEATURE
<222> LOCATION: (7)..(7)
<223> OTHER INFORMATION: Xaa may be Ala, Asn or Tyr
<220> FEATURE:
<221> NAME/KEY: MISC_FEATURE
<222> LOCATION: (8)..(8)
<223> OTHER INFORMATION: Xaa may be Ala, Gly, Trp or Tyr
<220> FEATURE:
<221> NAME/KEY: MISC_FEATURE
<222> LOCATION: (9)..(9)
<223> OTHER INFORMATION: Xaa may be Ile or Met
<220> FEATURE:
<221> NAME/KEY: MISC_FEATURE
<222> LOCATION: (10)..(10)
<223> OTHER INFORMATION: Xaa may be His, Asn or Ser

<400> SEQUENCE: 27

Gly Phe Thr Xaa Ser Xaa Xaa Xaa Xaa Xaa
1 5 10

<210> SEQ ID NO 28
<211> LENGTH: 10
<212> TYPE: PRT
<213> ORGANISM: Homo sapiens

<400> SEQUENCE: 28

Gly Phe Thr Phe Ser Asp Ala Trp Ile Asn
1 5 10

<210> SEQ ID NO 29
<211> LENGTH: 10
<212> TYPE: PRT
<213> ORGANISM: Homo sapiens

<400> SEQUENCE: 29

Gly Phe Thr Phe Ser Asp Tyr Tyr Met Ser
1 5 10

<210> SEQ ID NO 30
<211> LENGTH: 10

<212> TYPE: PRT
<213> ORGANISM: Homo sapiens

<400> SEQUENCE: 30

Gly Phe Thr Phe Ser Ser Tyr Ala Met His
1 5 10

<210> SEQ ID NO 31
<211> LENGTH: 10
<212> TYPE: PRT
<213> ORGANISM: Homo sapiens

<400> SEQUENCE: 31

Gly Phe Thr Phe Ser Ser Tyr Ala Met Ser
1 5 10

<210> SEQ ID NO 32
<211> LENGTH: 10
<212> TYPE: PRT
<213> ORGANISM: Homo sapiens

<400> SEQUENCE: 32

Gly Phe Thr Phe Ser Ser Tyr Gly Met His
1 5 10

<210> SEQ ID NO 33
<211> LENGTH: 10
<212> TYPE: PRT
<213> ORGANISM: Homo sapiens

<400> SEQUENCE: 33

Gly Phe Thr Phe Ser Ser Tyr Trp Met Ser
1 5 10

<210> SEQ ID NO 34
<211> LENGTH: 10
<212> TYPE: PRT
<213> ORGANISM: Homo sapiens

<400> SEQUENCE: 34

Gly Phe Thr Val Ser Ser Asn Tyr Met Ser
1 5 10

<210> SEQ ID NO 35
<211> LENGTH: 16
<212> TYPE: PRT
<213> ORGANISM: Homo sapiens

<400> SEQUENCE: 35

Ala Ile Ser Gly Ser Gly Gly Ser Thr Tyr Ala Asp Ser Val Lys Gly
1 5 10 15

<210> SEQ ID NO 36
<211> LENGTH: 17
<212> TYPE: PRT
<213> ORGANISM: Homo sapiens

<400> SEQUENCE: 36

Asn Ile Lys Gln Asp Gly Ser Glu Lys Tyr Tyr Ala Asp Ser Val Lys
1 5 10 15

Gly

<210> SEQ ID NO 37
<211> LENGTH: 17
<212> TYPE: PRT

<213> ORGANISM: Homo sapiens

<400> SEQUENCE: 37

Asn Ile Lys Gln Asp Gly Ser Glu Lys Tyr Tyr Val Asp Ser Val Lys
1 5 10 15

Gly

<210> SEQ ID NO 38
<211> LENGTH: 19
<212> TYPE: PRT
<213> ORGANISM: Homo sapiens

<400> SEQUENCE: 38

Arg Ile Lys Ser Lys Thr Asp Gly Gly Thr Thr Asp Tyr Ala Ala Pro
1 5 10 15

Val Lys Gly

<210> SEQ ID NO 39
<211> LENGTH: 17
<212> TYPE: PRT
<213> ORGANISM: Homo sapiens

<400> SEQUENCE: 39

Val Ile Trp Tyr Asp Gly Ser Asn Lys Tyr Tyr Ala Asp Ser Val Lys
1 5 10 15

Gly

<210> SEQ ID NO 40
<211> LENGTH: 17
<212> TYPE: PRT
<213> ORGANISM: Homo sapiens

<400> SEQUENCE: 40

Val Ile Ser Tyr Asp Gly Ser Asn Lys Tyr Tyr Ala Asp Ser Val Lys
1 5 10 15

Gly

<210> SEQ ID NO 41
<211> LENGTH: 16
<212> TYPE: PRT
<213> ORGANISM: Homo sapiens

<400> SEQUENCE: 41

Val Ile Tyr Ser Gly Gly Ser Thr Tyr Tyr Ala Asp Ser Val Lys Gly
1 5 10 15

<210> SEQ ID NO 42
<211> LENGTH: 17
<212> TYPE: PRT
<213> ORGANISM: Homo sapiens

<400> SEQUENCE: 42

Tyr Ile Ser Ser Ser Gly Gly Thr Ile Tyr Tyr Ala Asp Ser Val Lys
1 5 10 15

Gly

<210> SEQ ID NO 43
<211> LENGTH: 17
<212> TYPE: PRT
<213> ORGANISM: Homo sapiens

<400> SEQUENCE: 43

Tyr Ile Ser Ser Ser Ser Ser Tyr Thr Asn Tyr Ala Asp Ser Val Lys
1 5 10 15

Gly

<210> SEQ ID NO 44
<211> LENGTH: 12
<212> TYPE: PRT
<213> ORGANISM: Homo sapiens

<400> SEQUENCE: 44

Ala Met Val Arg Gly Val Thr Lys Pro Phe Asp Tyr
1 5 10

<210> SEQ ID NO 45
<211> LENGTH: 12
<212> TYPE: PRT
<213> ORGANISM: Homo sapiens

<400> SEQUENCE: 45

Ala Tyr Tyr Tyr Tyr Asp Ser Ser Gly Tyr Gly Tyr
1 5 10

<210> SEQ ID NO 46
<211> LENGTH: 14
<212> TYPE: PRT
<213> ORGANISM: Homo sapiens

<400> SEQUENCE: 46

Asp Leu Val Asp Tyr Asp Ser Ser Gly Tyr Tyr Pro Asp Tyr
1 5 10

<210> SEQ ID NO 47
<211> LENGTH: 20
<212> TYPE: PRT
<213> ORGANISM: Homo sapiens

<400> SEQUENCE: 47

Asp Arg Gly Phe Gly Tyr Cys Ser Ser Thr Ser Cys His Thr Glu Asp
1 5 10 15

Ala Phe Asp Ile
20

<210> SEQ ID NO 48
<211> LENGTH: 19
<212> TYPE: PRT
<213> ORGANISM: Homo sapiens

<400> SEQUENCE: 48

Asp Arg His Pro Gly Tyr Cys Ser Ser Thr Ser Cys Phe Val Arg Tyr
1 5 10 15

Phe Asp Tyr

<210> SEQ ID NO 49
<211> LENGTH: 17
<212> TYPE: PRT
<213> ORGANISM: Homo sapiens

<400> SEQUENCE: 49

Asp Arg Arg Gly Ile Ala Ala Thr Ala Gly Tyr Tyr Tyr Gly Met Asp
1 5 10 15

Val

<210> SEQ ID NO 50

<211> LENGTH: 20
<212> TYPE: PRT
<213> ORGANISM: Homo sapiens

<400> SEQUENCE: 50

```
Asp Trp Gly Ile Val Asp Thr Ala Met Val Pro Tyr Tyr Tyr Tyr Tyr
1               5                   10                  15

Gly Met Asp Val
            20
```

<210> SEQ ID NO 51
<211> LENGTH: 16
<212> TYPE: PRT
<213> ORGANISM: Homo sapiens

<400> SEQUENCE: 51

```
Glu Ala Pro Ser Ser Gly Trp Tyr Pro Tyr Tyr Tyr Tyr Met Asp Val
1               5                   10                  15
```

<210> SEQ ID NO 52
<211> LENGTH: 22
<212> TYPE: PRT
<213> ORGANISM: Homo sapiens

<400> SEQUENCE: 52

```
Glu His Arg Gly Gly Tyr Tyr Asp Ile Leu Thr Gly Tyr Thr Lys His
1               5                   10                  15

Gly Gly Ser Asn Asp Tyr
            20
```

<210> SEQ ID NO 53
<211> LENGTH: 8
<212> TYPE: PRT
<213> ORGANISM: Homo sapiens

<400> SEQUENCE: 53

```
Glu Arg Tyr Tyr Tyr Met Asp Val
1               5
```

<210> SEQ ID NO 54
<211> LENGTH: 15
<212> TYPE: PRT
<213> ORGANISM: Homo sapiens

<400> SEQUENCE: 54

```
Gly Gly Asp Tyr Tyr Asp Ser Ser Gly Tyr Tyr Leu Pro Trp Tyr
1               5                   10                  15
```

<210> SEQ ID NO 55
<211> LENGTH: 17
<212> TYPE: PRT
<213> ORGANISM: Homo sapiens

<400> SEQUENCE: 55

```
Gly Thr Asp Thr Glu Ser Val Ala Ala Pro Tyr Tyr Tyr Tyr Met Asp
1               5                   10                  15

Val
```

<210> SEQ ID NO 56
<211> LENGTH: 8
<212> TYPE: PRT
<213> ORGANISM: Homo sapiens

<400> SEQUENCE: 56

Gly Val Ala Gly Arg Phe Asp Tyr
1 5

<210> SEQ ID NO 57
<211> LENGTH: 12
<212> TYPE: PRT
<213> ORGANISM: Homo sapiens

<400> SEQUENCE: 57

Gly Val Val Pro Ala Ala Glu Ser Trp Phe Asp Pro
1 5 10

<210> SEQ ID NO 58
<211> LENGTH: 17
<212> TYPE: PRT
<213> ORGANISM: Homo sapiens

<400> SEQUENCE: 58

Lys Asp Gly Ser Gly Ser Tyr Tyr His Tyr Tyr Tyr Tyr Val Met Asp
1 5 10 15

Val

<210> SEQ ID NO 59
<211> LENGTH: 13
<212> TYPE: PRT
<213> ORGANISM: Homo sapiens

<400> SEQUENCE: 59

Lys Thr Tyr Tyr Tyr Tyr Asp Ser Ser Gly Tyr Gly Tyr
1 5 10

<210> SEQ ID NO 60
<211> LENGTH: 13
<212> TYPE: PRT
<213> ORGANISM: Homo sapiens

<400> SEQUENCE: 60

Gln Asp Ile Ala Ala Ala Ala Pro Tyr Tyr Phe Asp Tyr
1 5 10

<210> SEQ ID NO 61
<211> LENGTH: 10
<212> TYPE: PRT
<213> ORGANISM: Homo sapiens

<400> SEQUENCE: 61

Ser Gly Ala Ser Leu Arg Ala Phe Asp Ile
1 5 10

<210> SEQ ID NO 62
<211> LENGTH: 9
<212> TYPE: PRT
<213> ORGANISM: Homo sapiens

<400> SEQUENCE: 62

Ser Gly Tyr Tyr Tyr Pro Leu Asp Tyr
1 5

<210> SEQ ID NO 63
<211> LENGTH: 14
<212> TYPE: PRT
<213> ORGANISM: Homo sapiens

<400> SEQUENCE: 63

Tyr Cys Ser Ser Thr Ser Cys Ser Ser Glu Tyr Phe Gly His

-continued 1 5 10

<210> SEQ ID NO 64
<211> LENGTH: 15
<212> TYPE: PRT
<213> ORGANISM: Homo sapiens

<400> SEQUENCE: 64

Tyr Tyr Tyr Asp Ser Ser Ala Val Glu Gly Asp Ala Phe Asp Ile
1 5 10 15

<210> SEQ ID NO 65
<211> LENGTH: 12
<212> TYPE: PRT
<213> ORGANISM: Artificial
<220> FEATURE:
<223> OTHER INFORMATION: anti-alpha-Synuclein HCv Type 2, CDR1, consensus sequence
<220> FEATURE:
<221> NAME/KEY: MISC_FEATURE
<222> LOCATION: (10)..(10)
<223> OTHER INFORMATION: Xaa may be Ser or Tyr

<400> SEQUENCE: 65

Gly Gly Ser Ile Ser Ser Gly Gly Tyr Xaa Trp Ser
1 5 10

<210> SEQ ID NO 66
<211> LENGTH: 12
<212> TYPE: PRT
<213> ORGANISM: Homo sapiens

<400> SEQUENCE: 66

Gly Gly Ser Ile Ser Ser Gly Gly Tyr Ser Trp Ser
1 5 10

<210> SEQ ID NO 67
<211> LENGTH: 12
<212> TYPE: PRT
<213> ORGANISM: Homo sapiens

<400> SEQUENCE: 67

Gly Gly Ser Ile Ser Ser Gly Gly Tyr Tyr Trp Ser
1 5 10

<210> SEQ ID NO 68
<211> LENGTH: 16
<212> TYPE: PRT
<213> ORGANISM: Artificial
<220> FEATURE:
<223> OTHER INFORMATION: anti-alpha-Synuclein HCv Type 2, CDR2, consensus sequence
<220> FEATURE:
<221> NAME/KEY: MISC_FEATURE
<222> LOCATION: (4)..(4)
<223> OTHER INFORMATION: Xaa may be His or Tyr

<400> SEQUENCE: 68

Tyr Ile Tyr Xaa Ser Gly Ser Thr Tyr Tyr Asn Pro Ser Leu Lys Ser
1 5 10 15

<210> SEQ ID NO 69
<211> LENGTH: 16
<212> TYPE: PRT
<213> ORGANISM: Homo sapiens

<400> SEQUENCE: 69

Tyr Ile Tyr His Ser Gly Ser Thr Tyr Tyr Asn Pro Ser Leu Lys Ser 1 5 10 15

<210> SEQ ID NO 70
<211> LENGTH: 16
<212> TYPE: PRT
<213> ORGANISM: Homo sapiens

<400> SEQUENCE: 70

Tyr Ile Tyr Tyr Ser Gly Ser Thr Tyr Tyr Asn Pro Ser Leu Lys Ser
1 5 10 15

<210> SEQ ID NO 71
<211> LENGTH: 10
<212> TYPE: PRT
<213> ORGANISM: Homo sapiens

<400> SEQUENCE: 71

Ala Gly Tyr Tyr Tyr Tyr Tyr Met Asp Val
1 5 10

<210> SEQ ID NO 72
<211> LENGTH: 22
<212> TYPE: PRT
<213> ORGANISM: Homo sapiens

<400> SEQUENCE: 72

Ala His Pro Val Arg Gly Ser Gly Ser Tyr Tyr Asn Arg Asn Tyr Tyr
1 5 10 15

Tyr Tyr Tyr Met Asp Val
20

<210> SEQ ID NO 73
<211> LENGTH: 12
<212> TYPE: PRT
<213> ORGANISM: Homo sapiens

<400> SEQUENCE: 73

Gly Ser Arg Glu Gly Tyr Gly Asp Arg Ile Asp Tyr
1 5 10

<210> SEQ ID NO 74
<211> LENGTH: 21
<212> TYPE: PRT
<213> ORGANISM: Homo sapiens

<400> SEQUENCE: 74

Gly Thr Glu Tyr Cys Thr Asn Gly Ala Cys Tyr Met Gly Tyr Tyr Tyr
1 5 10 15

Tyr Tyr Met Asp Val
20

<210> SEQ ID NO 75
<211> LENGTH: 21
<212> TYPE: PRT
<213> ORGANISM: Homo sapiens

<400> SEQUENCE: 75

Gly Thr Glu Tyr Cys Thr Asn Gly Val Cys Tyr Met Gly Tyr Tyr Tyr
1 5 10 15

Tyr Tyr Met Asp Val
20

<210> SEQ ID NO 76
<211> LENGTH: 10

<212> TYPE: PRT
<213> ORGANISM: Homo sapiens

<400> SEQUENCE: 76

Gly Gly Thr Phe Ser Ser Tyr Ala Ile Ser
1 5 10

<210> SEQ ID NO 77
<211> LENGTH: 10
<212> TYPE: PRT
<213> ORGANISM: Homo sapiens

<400> SEQUENCE: 77

Gly Tyr Ile Ile Ala Asn Tyr Tyr Ile His
1 5 10

<210> SEQ ID NO 78
<211> LENGTH: 10
<212> TYPE: PRT
<213> ORGANISM: Homo sapiens

<400> SEQUENCE: 78

Gly Tyr Ile Ile Thr Asn Tyr Tyr Ile His
1 5 10

<210> SEQ ID NO 79
<211> LENGTH: 10
<212> TYPE: PRT
<213> ORGANISM: Homo sapiens

<400> SEQUENCE: 79

Gly Tyr Thr Phe Thr Gly Tyr Tyr Met His
1 5 10

<210> SEQ ID NO 80
<211> LENGTH: 10
<212> TYPE: PRT
<213> ORGANISM: Homo sapiens

<400> SEQUENCE: 80

Gly Tyr Thr Phe Thr Ser Tyr Tyr Met His
1 5 10

<210> SEQ ID NO 81
<211> LENGTH: 17
<212> TYPE: PRT
<213> ORGANISM: Artificial
<220> FEATURE:
<223> OTHER INFORMATION: anti-alpha-Synuclein HCv Type 3, CDR2,
consensus sequence
<220> FEATURE:
<221> NAME/KEY: MISC_FEATURE
<222> LOCATION: (1)..(1)
<223> OTHER INFORMATION: Xaa may be Gly, Ile or Trp
<220> FEATURE:
<221> NAME/KEY: MISC_FEATURE
<222> LOCATION: (3)..(3)
<223> OTHER INFORMATION: Xaa may be Ile, Asn or Thr
<220> FEATURE:
<221> NAME/KEY: MISC_FEATURE
<222> LOCATION: (5)..(5)
<223> OTHER INFORMATION: Xaa may be Ile, Asn or Ser
<220> FEATURE:
<221> NAME/KEY: MISC_FEATURE
<222> LOCATION: (6)..(6)
<223> OTHER INFORMATION: Xaa may be Phe, Gly, His or Ser
<220> FEATURE:
<221> NAME/KEY: MISC_FEATURE
<222> LOCATION: (8)..(8)
<223> OTHER INFORMATION: Xaa may be Ala, Gly, Ser or Thr
<220> FEATURE:
<221> NAME/KEY: MISC_FEATURE
<222> LOCATION: (9)..(9)
<223> OTHER INFORMATION: Xaa may be Ala or Thr
<220> FEATURE:
<221> NAME/KEY: MISC_FEATURE
<222> LOCATION: (10)..(10)
<223> OTHER INFORMATION: Xaa may be Asn or Ser

<400> SEQUENCE: 81

Xaa Ile Xaa Pro Xaa Xaa Gly Xaa Xaa Xaa Tyr Ala Gln Lys Phe Gln
1 5 10 15

Gly

<210> SEQ ID NO 82
<211> LENGTH: 17
<212> TYPE: PRT
<213> ORGANISM: Homo sapiens

<400> SEQUENCE: 82

Gly Ile Ile Pro Ile Phe Gly Thr Ala Asn Tyr Ala Gln Lys Phe Gln
1 5 10 15

Gly

<210> SEQ ID NO 83
<211> LENGTH: 17
<212> TYPE: PRT
<213> ORGANISM: Homo sapiens

<400> SEQUENCE: 83

Ile Ile Asn Pro Ser Gly Gly Ser Thr Ser Tyr Ala Gln Lys Phe Gln
1 5 10 15

Gly

<210> SEQ ID NO 84
<211> LENGTH: 17
<212> TYPE: PRT
<213> ORGANISM: Homo sapiens

<400> SEQUENCE: 84

Ile Ile Thr Pro Ser His Gly Ala Thr Asn Tyr Ala Gln Lys Phe Gln
1 5 10 15

Gly

<210> SEQ ID NO 85
<211> LENGTH: 17
<212> TYPE: PRT
<213> ORGANISM: Homo sapiens

<400> SEQUENCE: 85

Trp Ile Asn Pro Asn Ser Gly Gly Thr Asn Tyr Ala Gln Lys Phe Gln
1 5 10 15

Gly

<210> SEQ ID NO 86
<211> LENGTH: 18
<212> TYPE: PRT
<213> ORGANISM: Homo sapiens

<400> SEQUENCE: 86

Ala Lys Asp Tyr Asp Phe Trp Arg Gly Ser Thr Gly Met Arg Tyr Leu
1 5 10 15

Asp Val

<210> SEQ ID NO 87
<211> LENGTH: 19
<212> TYPE: PRT
<213> ORGANISM: Homo sapiens

<400> SEQUENCE: 87

Asp Lys Arg Cys Ser Ser Thr Ser Cys Gln Pro Tyr Tyr Tyr Tyr Tyr
1 5 10 15

Met Asp Val

<210> SEQ ID NO 88
<211> LENGTH: 16
<212> TYPE: PRT
<213> ORGANISM: Homo sapiens

<400> SEQUENCE: 88

Asp Ser Gly Ser Ser Gly Trp Tyr Val Pro Tyr Trp Tyr Phe Asp Leu
1 5 10 15

<210> SEQ ID NO 89
<211> LENGTH: 17
<212> TYPE: PRT
<213> ORGANISM: Homo sapiens

<400> SEQUENCE: 89

Pro Ile Gly Gly Gly Pro Ser Gly Trp Tyr Glu Thr Ser Cys Phe Asp
1 5 10 15

Pro

<210> SEQ ID NO 90
<211> LENGTH: 19
<212> TYPE: PRT
<213> ORGANISM: Homo sapiens

<400> SEQUENCE: 90

Thr Ser Tyr Gly Asp Ser Ser Ser Ser Ser Tyr Tyr Tyr Tyr Tyr Gly
1 5 10 15

Met Asp Val

<210> SEQ ID NO 91
<211> LENGTH: 10
<212> TYPE: PRT
<213> ORGANISM: Homo sapiens

<400> SEQUENCE: 91

Val Asp Tyr Ser Asn Tyr Val Val Asp Tyr
1 5 10

<210> SEQ ID NO 92
<211> LENGTH: 16
<212> TYPE: PRT
<213> ORGANISM: Homo sapiens

<400> SEQUENCE: 92

Arg Ser Ser Gln Ser Leu Leu His Ser Asn Gly Tyr Asn Tyr Leu Asp
1 5 10 15

<210> SEQ ID NO 93
<211> LENGTH: 7
<212> TYPE: PRT
<213> ORGANISM: Homo sapiens

<400> SEQUENCE: 93

Leu Gly Ser Asn Arg Ala Ser
1 5

<210> SEQ ID NO 94
<211> LENGTH: 9
<212> TYPE: PRT
<213> ORGANISM: Artificial
<220> FEATURE:
<223> OTHER INFORMATION: anti-alpha-Synuclein LCv Type 1, CDR3, consensus sequence
<220> FEATURE:
<221> NAME/KEY: MISC_FEATURE
<222> LOCATION: (6)..(6)
<223> OTHER INFORMATION: Xaa may not be present or may be Thr
<220> FEATURE:
<221> NAME/KEY: MISC_FEATURE
<222> LOCATION: (7)..(7)
<223> OTHER INFORMATION: Xaa may be Phe or Pro
<220> FEATURE:
<221> NAME/KEY: MISC_FEATURE
<222> LOCATION: (8)..(8)
<223> OTHER INFORMATION: Xaa may be Arg, Trp or Tyr

<400> SEQUENCE: 94

Met Gln Ala Leu Gln Xaa Xaa Xaa Thr
1 5

<210> SEQ ID NO 95
<211> LENGTH: 9
<212> TYPE: PRT
<213> ORGANISM: Homo sapiens

<400> SEQUENCE: 95

Met Gln Ala Leu Gln Thr Pro Arg Thr
1 5

<210> SEQ ID NO 96
<211> LENGTH: 9
<212> TYPE: PRT
<213> ORGANISM: Homo sapiens

<400> SEQUENCE: 96

Met Gln Ala Leu Gln Thr Pro Trp Thr
1 5

<210> SEQ ID NO 97
<211> LENGTH: 9
<212> TYPE: PRT
<213> ORGANISM: Homo sapiens

<400> SEQUENCE: 97

Met Gln Ala Leu Gln Thr Pro Tyr Thr
1 5

<210> SEQ ID NO 98
<211> LENGTH: 8
<212> TYPE: PRT
<213> ORGANISM: Homo sapiens

<400> SEQUENCE: 98

Met Gln Ala Thr Gln Phe Arg Thr
1 5

<210> SEQ ID NO 99
<211> LENGTH: 12
<212> TYPE: PRT
<213> ORGANISM: Artificial
<220> FEATURE:

<223> OTHER INFORMATION: anti-alpha-Synuclein LCv Type 2, CDR1,
consensus sequence
<220> FEATURE:
<221> NAME/KEY: MISC_FEATURE
<222> LOCATION: (9)..(9)
<223> OTHER INFORMATION: Xaa may not be present or may be Ser
<220> FEATURE:
<221> NAME/KEY: MISC_FEATURE
<222> LOCATION: (10)..(10)
<223> OTHER INFORMATION: Xaa may be Asn or Tyr

<400> SEQUENCE: 99

Arg Ala Ser Gln Ser Val Ser Ser Xaa Xaa Leu Ala
1 5 10

<210> SEQ ID NO 100
<211> LENGTH: 11
<212> TYPE: PRT
<213> ORGANISM: Homo sapiens

<400> SEQUENCE: 100

Arg Ala Ser Gln Ser Val Ser Ser Asn Leu Ala
1 5 10

<210> SEQ ID NO 101
<211> LENGTH: 12
<212> TYPE: PRT
<213> ORGANISM: Homo sapiens

<400> SEQUENCE: 101

Arg Ala Ser Gln Ser Val Ser Ser Ser Tyr Leu Ala
1 5 10

<210> SEQ ID NO 102
<211> LENGTH: 11
<212> TYPE: PRT
<213> ORGANISM: Homo sapiens

<400> SEQUENCE: 102

Arg Ala Ser Gln Ser Val Ser Ser Tyr Leu Ala
1 5 10

<210> SEQ ID NO 103
<211> LENGTH: 7
<212> TYPE: PRT
<213> ORGANISM: Artificial
<220> FEATURE:
<223> OTHER INFORMATION: anti-alpha-Synuclein LCv Type 2, CDR2,
consensus sequence
<220> FEATURE:
<221> NAME/KEY: MISC_FEATURE
<222> LOCATION: (1)..(1)
<223> OTHER INFORMATION: Xaa may be Asp or Gly
<220> FEATURE:
<221> NAME/KEY: MISC_FEATURE
<222> LOCATION: (4)..(4)
<223> OTHER INFORMATION: Xaa may be Asn, Ser or Thr

<400> SEQUENCE: 103

Xaa Ala Ser Xaa Arg Ala Thr
1 5

<210> SEQ ID NO 104
<211> LENGTH: 7
<212> TYPE: PRT
<213> ORGANISM: Homo sapiens

<400> SEQUENCE: 104

Asp Ala Ser Asn Arg Ala Thr 1 5

<210> SEQ ID NO 105
<211> LENGTH: 7
<212> TYPE: PRT
<213> ORGANISM: Homo sapiens

<400> SEQUENCE: 105

Gly Ala Ser Ser Arg Ala Thr
1 5

<210> SEQ ID NO 106
<211> LENGTH: 7
<212> TYPE: PRT
<213> ORGANISM: Homo sapiens

<400> SEQUENCE: 106

Gly Ala Ser Thr Arg Ala Thr
1 5

<210> SEQ ID NO 107
<211> LENGTH: 9
<212> TYPE: PRT
<213> ORGANISM: Homo sapiens

<400> SEQUENCE: 107

Gln Gln Arg Ser Asn Trp Pro Pro Thr
1 5

<210> SEQ ID NO 108
<211> LENGTH: 10
<212> TYPE: PRT
<213> ORGANISM: Homo sapiens

<400> SEQUENCE: 108

Gln Gln Arg Ser Asn Trp Pro Pro Tyr Thr
1 5 10

<210> SEQ ID NO 109
<211> LENGTH: 8
<212> TYPE: PRT
<213> ORGANISM: Homo sapiens

<400> SEQUENCE: 109

Gln Gln Tyr Gly Ser Ser Trp Thr
1 5

<210> SEQ ID NO 110
<211> LENGTH: 9
<212> TYPE: PRT
<213> ORGANISM: Homo sapiens

<400> SEQUENCE: 110

Gln Gln Tyr Asn Asn Trp Pro Leu Thr
1 5

<210> SEQ ID NO 111
<211> LENGTH: 11
<212> TYPE: PRT
<213> ORGANISM: Homo sapiens

<400> SEQUENCE: 111

Gln Gln Tyr Asn Asn Trp Pro Pro Met Tyr Thr
1 5 10

-continued

```
<210> SEQ ID NO 112
<211> LENGTH: 9
<212> TYPE: PRT
<213> ORGANISM: Homo sapiens

<400> SEQUENCE: 112

Gln Gln Tyr Asn Asn Trp Pro Arg Thr
1               5


<210> SEQ ID NO 113
<211> LENGTH: 8
<212> TYPE: PRT
<213> ORGANISM: Homo sapiens

<400> SEQUENCE: 113

Gln Gln Tyr Asn Asn Trp Trp Thr
1               5


<210> SEQ ID NO 114
<211> LENGTH: 8
<212> TYPE: PRT
<213> ORGANISM: Homo sapiens

<400> SEQUENCE: 114

Gln Gln Tyr Asn Asn Trp Tyr Thr
1               5


<210> SEQ ID NO 115
<211> LENGTH: 11
<212> TYPE: PRT
<213> ORGANISM: Artificial
<220> FEATURE:
<223> OTHER INFORMATION: anti-alpha-Synuclein LCv Type 3, CDR1,
      consensus sequence
<220> FEATURE:
<221> NAME/KEY: MISC_FEATURE
<222> LOCATION: (2)..(2)
<223> OTHER INFORMATION: Xaa may be Ala or Met
<220> FEATURE:
<221> NAME/KEY: MISC_FEATURE
<222> LOCATION: (5)..(5)
<223> OTHER INFORMATION: Xaa may be Gly or Ser
<220> FEATURE:
<221> NAME/KEY: MISC_FEATURE
<222> LOCATION: (7)..(7)
<223> OTHER INFORMATION: Xaa may be Arg or Ser
<220> FEATURE:
<221> NAME/KEY: MISC_FEATURE
<222> LOCATION: (8)..(8)
<223> OTHER INFORMATION: Xaa may be Asn or Ser
<220> FEATURE:
<221> NAME/KEY: MISC_FEATURE
<222> LOCATION: (9)..(9)
<223> OTHER INFORMATION: Xaa may be Asp, Trp or Tyr
<220> FEATURE:
<221> NAME/KEY: MISC_FEATURE
<222> LOCATION: (11)..(11)
<223> OTHER INFORMATION: Xaa may be Ala or Gly

<400> SEQUENCE: 115

Arg Xaa Ser Gln Xaa Ile Xaa Xaa Xaa Leu Xaa
1               5                   10


<210> SEQ ID NO 116
<211> LENGTH: 11
<212> TYPE: PRT
<213> ORGANISM: Homo sapiens

<400> SEQUENCE: 116

Arg Ala Ser Gln Gly Ile Arg Asn Asp Leu Gly
1               5                   10
```

<210> SEQ ID NO 117
<211> LENGTH: 11
<212> TYPE: PRT
<213> ORGANISM: Homo sapiens

<400> SEQUENCE: 117

Arg Ala Ser Gln Gly Ile Ser Asn Tyr Leu Ala
1 5 10

<210> SEQ ID NO 118
<211> LENGTH: 11
<212> TYPE: PRT
<213> ORGANISM: Homo sapiens

<400> SEQUENCE: 118

Arg Ala Ser Gln Gly Ile Ser Ser Trp Leu Ala
1 5 10

<210> SEQ ID NO 119
<211> LENGTH: 11
<212> TYPE: PRT
<213> ORGANISM: Homo sapiens

<400> SEQUENCE: 119

Arg Ala Ser Gln Gly Ile Ser Ser Tyr Leu Ala
1 5 10

<210> SEQ ID NO 120
<211> LENGTH: 11
<212> TYPE: PRT
<213> ORGANISM: Homo sapiens

<400> SEQUENCE: 120

Arg Ala Ser Gln Ser Ile Ser Ser Trp Leu Ala
1 5 10

<210> SEQ ID NO 121
<211> LENGTH: 11
<212> TYPE: PRT
<213> ORGANISM: Homo sapiens

<400> SEQUENCE: 121

Arg Met Ser Gln Gly Ile Ser Ser Trp Leu Ala
1 5 10

<210> SEQ ID NO 122
<211> LENGTH: 11
<212> TYPE: PRT
<213> ORGANISM: Homo sapiens

<400> SEQUENCE: 122

Arg Met Ser Gln Gly Ile Ser Ser Tyr Leu Ala
1 5 10

<210> SEQ ID NO 123
<211> LENGTH: 7
<212> TYPE: PRT
<213> ORGANISM: Homo sapiens

<400> SEQUENCE: 123

Ala Ala Ser Ser Leu Gln Ser
1 5

<210> SEQ ID NO 124

<211> LENGTH: 7
<212> TYPE: PRT
<213> ORGANISM: Homo sapiens

<400> SEQUENCE: 124

Ala Ala Ser Thr Leu Gln Ser
1 5

<210> SEQ ID NO 125
<211> LENGTH: 7
<212> TYPE: PRT
<213> ORGANISM: Homo sapiens

<400> SEQUENCE: 125

Ala Ala Ser Thr Leu Val Ser
1 5

<210> SEQ ID NO 126
<211> LENGTH: 7
<212> TYPE: PRT
<213> ORGANISM: Homo sapiens

<400> SEQUENCE: 126

Asp Ala Ser Asn Leu Glu Thr
1 5

<210> SEQ ID NO 127
<211> LENGTH: 7
<212> TYPE: PRT
<213> ORGANISM: Homo sapiens

<400> SEQUENCE: 127

Lys Ala Ser Ser Leu Glu Ser
1 5

<210> SEQ ID NO 128
<211> LENGTH: 9
<212> TYPE: PRT
<213> ORGANISM: Homo sapiens

<400> SEQUENCE: 128

Leu Gly Asp Tyr Asn Tyr Pro Tyr Thr
1 5

<210> SEQ ID NO 129
<211> LENGTH: 9
<212> TYPE: PRT
<213> ORGANISM: Homo sapiens

<400> SEQUENCE: 129

Leu Gln Asp Asn Asn Tyr Pro Arg Thr
1 5

<210> SEQ ID NO 130
<211> LENGTH: 9
<212> TYPE: PRT
<213> ORGANISM: Homo sapiens

<400> SEQUENCE: 130

Leu Gln Asp Tyr Asn Tyr Pro Tyr Thr
1 5

<210> SEQ ID NO 131
<211> LENGTH: 9
<212> TYPE: PRT
<213> ORGANISM: Homo sapiens

<400> SEQUENCE: 131

Leu Gln His Asn Ser Tyr Pro Phe Thr
1               5

<210> SEQ ID NO 132
<211> LENGTH: 9
<212> TYPE: PRT
<213> ORGANISM: Homo sapiens

<400> SEQUENCE: 132

Leu Gln His Asn Ser Tyr Pro Val Thr
1               5

<210> SEQ ID NO 133
<211> LENGTH: 9
<212> TYPE: PRT
<213> ORGANISM: Homo sapiens

<400> SEQUENCE: 133

Gln Gln Ala Asn Ser Phe Pro Ile Thr
1               5

<210> SEQ ID NO 134
<211> LENGTH: 9
<212> TYPE: PRT
<213> ORGANISM: Homo sapiens

<400> SEQUENCE: 134

Gln Gln Ala Asn Ser Phe Pro Leu Thr
1               5

<210> SEQ ID NO 135
<211> LENGTH: 10
<212> TYPE: PRT
<213> ORGANISM: Homo sapiens

<400> SEQUENCE: 135

Gln Gln Leu Asn Ser Tyr Pro Leu Phe Thr
1               5                   10

<210> SEQ ID NO 136
<211> LENGTH: 10
<212> TYPE: PRT
<213> ORGANISM: Homo sapiens

<400> SEQUENCE: 136

Gln Gln Tyr Asp Asn Leu Pro Pro Phe Thr
1               5                   10

<210> SEQ ID NO 137
<211> LENGTH: 9
<212> TYPE: PRT
<213> ORGANISM: Homo sapiens

<400> SEQUENCE: 137

Gln Gln Tyr Asn Ser Tyr Pro Val Thr
1               5

<210> SEQ ID NO 138
<211> LENGTH: 9
<212> TYPE: PRT
<213> ORGANISM: Homo sapiens

<400> SEQUENCE: 138

-continued

Gln Gln Tyr Asn Ser Tyr Pro Trp Thr
1 5

<210> SEQ ID NO 139
<211> LENGTH: 9
<212> TYPE: PRT
<213> ORGANISM: Homo sapiens

<400> SEQUENCE: 139

Gln Gln Tyr Asn Ser Tyr Pro Tyr Thr
1 5

<210> SEQ ID NO 140
<211> LENGTH: 11
<212> TYPE: PRT
<213> ORGANISM: Homo sapiens

<400> SEQUENCE: 140

Gln Gln Tyr Asn Ser Tyr Ser Arg Lys Tyr Thr
1 5 10

<210> SEQ ID NO 141
<211> LENGTH: 9
<212> TYPE: PRT
<213> ORGANISM: Homo sapiens

<400> SEQUENCE: 141

Leu Gln Asp Tyr Asn Tyr Pro Leu Thr
1 5

<210> SEQ ID NO 142
<211> LENGTH: 9
<212> TYPE: PRT
<213> ORGANISM: Homo sapiens

<400> SEQUENCE: 142

Gln Gln Tyr Asn Ser Tyr Leu Tyr Thr
1 5

<210> SEQ ID NO 143
<211> LENGTH: 9
<212> TYPE: PRT
<213> ORGANISM: Homo sapiens

<400> SEQUENCE: 143

Gln Gln Leu Asn Ser Tyr Pro Arg Thr
1 5

<210> SEQ ID NO 144
<211> LENGTH: 9
<212> TYPE: PRT
<213> ORGANISM: Homo sapiens

<400> SEQUENCE: 144

Leu Arg Asp Tyr Asn Tyr Pro Leu Thr
1 5

<210> SEQ ID NO 145
<211> LENGTH: 14
<212> TYPE: PRT
<213> ORGANISM: Homo sapiens

<400> SEQUENCE: 145

Arg Leu Thr Glu Glu Lys Gly Trp Met Tyr Leu Gly Tyr Thr
1 5 10

<210> SEQ ID NO 146
<211> LENGTH: 10
<212> TYPE: PRT
<213> ORGANISM: Homo sapiens

<400> SEQUENCE: 146

Gln Gln Arg Ser Asn Trp Pro Pro Ile Thr
1 5 10

<210> SEQ ID NO 147
<211> LENGTH: 9
<212> TYPE: PRT
<213> ORGANISM: Homo sapiens

<400> SEQUENCE: 147

Gln Gln Tyr Gly Ser Ser Pro Arg Thr
1 5

<210> SEQ ID NO 148
<211> LENGTH: 118
<212> TYPE: PRT
<213> ORGANISM: Homo sapiens

<400> SEQUENCE: 148

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Trp Thr Phe Gly Gln Gly Thr Lys Val Glu Ile Lys
100 105 110

Arg Thr Val Ala Ala Pro
115

<210> SEQ ID NO 149
<211> LENGTH: 118
<212> TYPE: PRT
<213> ORGANISM: Homo sapiens

<400> SEQUENCE: 149

Asp Ile Val Met Thr Gln Thr Pro Leu Ser Ser Pro Val Thr Leu Gly
1 5 10 15

Gln Pro Ala Ser Ile Ser Cys Arg Ser Ser Gln Ser Leu Val His Ser
20 25 30

Asp Gly Asn Thr Tyr Leu Ser Trp Leu Gln Gln Arg Pro Gly Gln Pro
35 40 45

Pro Arg Leu Leu Ile Tyr Lys Ile Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Glu Asp Val Gly Val Tyr Tyr Cys Met Gln Ala
85 90 95

-continued

```
Leu Gln Thr Pro Tyr Thr Phe Gly Gln Gly Thr Lys Leu Glu Ile Lys
            100                 105                 110

Arg Thr Val Ala Ala Pro
        115


<210> SEQ ID NO 150
<211> LENGTH: 124
<212> TYPE: PRT
<213> ORGANISM: Homo sapiens

<400> SEQUENCE: 150

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Val Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Asn Cys Gly Cys Thr Ile Cys Leu His Leu Pro
        115                 120


<210> SEQ ID NO 151
<211> LENGTH: 124
<212> TYPE: PRT
<213> ORGANISM: Homo sapiens

<400> SEQUENCE: 151

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Tyr Gln
            100                 105                 110

Thr Asn Cys Gly Cys Thr Ile Cys Leu His Leu Pro
        115                 120


<210> SEQ ID NO 152
<211> LENGTH: 10
<212> TYPE: PRT
<213> ORGANISM: Artificial
<220> FEATURE:
<223> OTHER INFORMATION: decamer peptide spot No. 1

<400> SEQUENCE: 152
```

Met Asp Val Phe Met Lys Gly Leu Ser Lys
1 5 10

<210> SEQ ID NO 153
<211> LENGTH: 10
<212> TYPE: PRT
<213> ORGANISM: Artificial
<220> FEATURE:
<223> OTHER INFORMATION: decamer peptide spot No. 7

<400> SEQUENCE: 153

Val Leu Tyr Val Gly Ser Lys Thr Lys Glu
1 5 10

<210> SEQ ID NO 154
<211> LENGTH: 10
<212> TYPE: PRT
<213> ORGANISM: Artificial
<220> FEATURE:
<223> OTHER INFORMATION: decamer peptide spot No. 13

<400> SEQUENCE: 154

Gly Val Thr Ala Val Ala Gln Lys Thr Asn
1 5 10

<210> SEQ ID NO 155
<211> LENGTH: 10
<212> TYPE: PRT
<213> ORGANISM: Artificial
<220> FEATURE:
<223> OTHER INFORMATION: decamer peptide spot No. 16

<400> SEQUENCE: 155

Ala Thr Gly Phe Val Lys Lys Asp Gln Leu
1 5 10

<210> SEQ ID NO 156
<211> LENGTH: 10
<212> TYPE: PRT
<213> ORGANISM: Artificial
<220> FEATURE:
<223> OTHER INFORMATION: decamer peptide spot No. 31

<400> SEQUENCE: 156

Val Leu Tyr Val Gly Ser Lys Met Lys Glu
1 5 10

<210> SEQ ID NO 157
<211> LENGTH: 10
<212> TYPE: PRT
<213> ORGANISM: Artificial
<220> FEATURE:
<223> OTHER INFORMATION: decamer peptide spot No. 49

<400> SEQUENCE: 157

Met Met Val Gly Lys Ser Asp Leu Lys Phe
1 5 10

<210> SEQ ID NO 158
<211> LENGTH: 10
<212> TYPE: PRT
<213> ORGANISM: Artificial
<220> FEATURE:
<223> OTHER INFORMATION: decamer peptide spot No. 50

<400> SEQUENCE: 158

Leu Glu Ser Val Gly Ala Lys Val Lys Gly
1 5 10

<210> SEQ ID NO 159
<211> LENGTH: 10
<212> TYPE: PRT
<213> ORGANISM: Artificial
<220> FEATURE:
<223> OTHER INFORMATION: decamer peptide spot No. 55

<400> SEQUENCE: 159

Val Tyr Ser Val Leu Lys Lys Glu Thr Gly
1               5                   10

<210> SEQ ID NO 160
<211> LENGTH: 10
<212> TYPE: PRT
<213> ORGANISM: Artificial
<220> FEATURE:
<223> OTHER INFORMATION: decamer peptide spot No. 64

<400> SEQUENCE: 160

Leu Lys Phe Thr Lys Asp Val Gln Gly Ala
1               5                   10

<210> SEQ ID NO 161
<211> LENGTH: 6
<212> TYPE: PRT
<213> ORGANISM: Artificial
<220> FEATURE:
<223> OTHER INFORMATION: hexamer peptide spot No. 77

<400> SEQUENCE: 161

Val Thr Ala Val Ala Gln
1               5

<210> SEQ ID NO 162
<211> LENGTH: 6
<212> TYPE: PRT
<213> ORGANISM: Artificial
<220> FEATURE:
<223> OTHER INFORMATION: hexamer peptide spot No. 83

<400> SEQUENCE: 162

Thr Gly Phe Val Lys Lys
1               5

<210> SEQ ID NO 163
<211> LENGTH: 6
<212> TYPE: PRT
<213> ORGANISM: Artificial
<220> FEATURE:
<223> OTHER INFORMATION: hexamer peptide spot No. 95

<400> SEQUENCE: 163

Thr Gly Met Val Lys Lys
1               5

<210> SEQ ID NO 164
<211> LENGTH: 6
<212> TYPE: PRT
<213> ORGANISM: Artificial
<220> FEATURE:
<223> OTHER INFORMATION: hexamer peptide spot No. 107

<400> SEQUENCE: 164

Lys Thr Lys Gly Phe Val
1               5

NATURALLY OCCURRING AUTOANTIBODIES AGAINST ALPHA-SYNUCLEIN THAT INHIBIT THE AGGREGATION AND CYTOTOXICITY OF ALPHA-SYNUCLEIN

CROSS REFERENCE TO RELATED APPLICATION

This application is a 35 U.S.C. 371 National Phase Entry Application from PCT/EP2011/053188, filed Mar. 3, 2011, which claims the benefit of European Patent Application No. 10155373.3 filed on Mar. 3, 2010, the disclosure of which is incorporated herein in its entirety by reference.

REFERENCE TO A SEQUENCE LISTING

The present application includes a Sequence Listing filed in electronic format. The Sequence Listing is entitled "2923-1172_ST25.txt" created on Nov. 9, 2012, and is 42,000 bytes in size. The information in the electronic format of the Sequence Listing is part of the present application and is incorporated herein by reference in its entirety.

The present invention refers to human antibodies which are directed against α-Synuclein (α-Syn) and their use in medicine and diagnosis.

Parkinson's disease (PD) is the second most common neurodegenerative disorder globally as it affects about 1% of the population over 65 years old worldwide. It is clinically characterized by resting tremor, slowness of movement, muscular rigidity and impairment of postural reflexes. The progressive loss of dopaminergic neurons in the substantia nigra and formation of fibrillar cytoplasmic inclusions termed Lewy bodies (LBs) and Lewy neurites are the neuropathological hallmarks of PD.

α-Synuclein (α-Syn) has been identified as the major component of such inclusions and it is found in the brains of PD patients and patients with other degenerative disorders such as the LB variant of Alzheimer's disease, dementia with LBs and both glial and neuronal cytoplasmic inclusions of multiple system atrophy. α-Syn has become a primary target of interest both because point mutations in the α-Synuclein gene and dosage effects caused by gene triplication have been linked to familial PD and because over-expression of α-Syn in neuronal cell lines and transgenic mice has been shown to lead to the formation of similar inclusions.

α-Syn consists of 140 amino acids, primarily expressed at presynaptic terminals in the central nervous system. It is divided into three distinct regions. The N-terminal region contains six imperfect repeats of the consensus sequence KGKEGV which may facilitate protein-protein interactions. The central region is known as the non-amyloid component ("NAC region") and may be essential for the aggregation of the peptide. The acidic C-terminal region is most likely responsible for the chaperone function of α-Syn. Though the specific role of α-Syn is still unknown, ample evidence suggests that over-expression disturbs normal cell function, resulting in decreased neurite outgrowth and cell adhesion. The mechanism that leads to the accumulation of α-Syn and subsequent neurodegeneration is still subject to ongoing research. Abnormal accumulation of α-Syn oligomers in the synaptic terminals and axons is now believed to be a key event in the pathogenesis of PD. Current research is focused on finding new approaches aiming at the reduction of abnormal accumulation of α-Syn.

In recent years, one effective approach in reducing neuronal accumulation of α-Syn aggregates has been immunization. It was hypothesized to have a potential role in the treatment of PD. One group was able to show that active immunization against human α-Syn resulted in a significant reduction of α-Syn aggregates in neuronal cell bodies and synapses of immunoresponsive transgenic mice as compared to untreated animals (Masliah et al., 2005). More recently, a human single-chain antibody fragment against oligomeric α-Syn was isolated from a phage display antibody library. This antibody fragment was able to bind oligomeric forms of α-Syn and inhibited both aggregation and toxicity of α-Syn in vitro (Emadi et al., 2007).

We were able to identify and isolate naturally occurring autoantibodies that bind to α-Syn (α-Syn-Abs) from human sera and from commercial IgG preparations (IVIG). These autoantibodies may be involved in the metabolism and clearance of α-Syn oligomers. Thus, a treatment with α-Syn-autoantibodies may be a beneficial therapeutic approach for PD patients.

Thus, a first aspect of the invention is a human antibody which is directed against an epitope between amino acids 60-100, for example between amino acids 60-95, or between amino acids 73-82 and/or between amino acids 91-100, particularly between amino acids 74-79 and/or between amino acids 92-97, of human α-Synuclein (α-Syn) or a fragment of such an antibody.

The antibody is suitable for use in medicine, particularly human medicine, more particularly for the treatment of neurodegenerative disorder such as Parkinson's disease. Furthermore, the antibody is suitable for use as a diagnostic agent, particularly as an agent for the diagnosis of a neurodegenerative disorder, such as Parkinson's disease.

A further aspect of the invention is a nucleic acid molecule encoding the antibody optionally in operative linkage to an expression control sequence.

A further aspect of the present invention is a recombinant cell which comprises the nucleic acid molecule. The cell may be used for the preparation of the antibody.

Still a further aspect of the present invention is a pharmaceutical composition comprising the antibody, the nucleic acid molecule or the recombinant cell together with a pharmaceutically acceptable carrier.

Still a further aspect of the present invention is a method for the treatment of a neurodegenerative disorder, comprising administering an antibody as described above to a subject, particularly a human subject in need thereof. This subject is suffering from a neurodegenerative disorder, such as Parkinson's disease or in risk of developing a neurodegenerative disorder, such as Parkinson's disease.

The present invention refers to a human antibody directed against α-Syn or a fragment thereof. The term "human antibody" encompasses fully human or humanized antibodies. Human antibodies may be prepared from genetically engineered animals, e.g. animals comprising a xenogenic immune system or from antibody display libraries according to known techniques. Humanized antibodies may be prepared by humanization of monoclonal antibodies according to known techniques.

Preferably, the human antibody of the invention is a naturally occurring human auto-antibody. Such an antibody may be isolated from sera of human donors or from commercial immunoglobulin preparations such as IVIG by immunochromatography with immobilized α-Syn. A human autoantibody preparation may be heterogeneous or homogenous. A heterogeneous preparation of autoantibodies may comprise a plurality of different autoantibody species. Such a preparation is obtainable by isolation from the sera of human donors, e.g. by immunochromatography as described above. A homogeneous autoantibody preparation may be obtained by recombinant manufacture of a single autoantibody species as herein described in detail below.

The inventors found that IgG specific for α-Syn can be isolated from peripheral human blood. Thus, actively anti-α-Syn IgG secreting cells of the B-cell lineage must be circulating within the blood and lymphatic system. Moreover, B-cells presenting anti-α-Syn on their cell surface must also be part of the blood B-cell system. Each of those anti-α-Syn B-cells is producing only one single specific antibody, which is translated from two separate mRNAs: one being the rearranged transcript displaying the antibody heavy chain and the other displaying the light chain. These mRNA molecules contain all the information required for the generation of anti-α-Syn antibodies. After preparing RNA from B-cells, the mRNA within the sample can be used as substrate for cDNA preparation which then can be used as template for "universal" IgG specific PCR reactions.

A "universal" but specific PCR can be achieved by choosing up-stream primers within the leader region of the IgG which do not discriminate for the antibody nucleotide sequence amplified, but differ significantly from sequences found in other cDNA than IgG related ones. The downstream primer may be situated at the beginning of the constant domain of the heavy or the light chain. Within these regions, conserved nucleotide sequences can be found, which allow for an immunoglobulin subtype specific—but CDR independent—amplification of the Ig cDNA nucleotide sequence.

To get access to an optimal IgG mRNA substrate, RNA may be isolated from B-cells derived from blood donation buffy coats. After preparation of the peripheral blood mononuclear cells (PBMC), B-cells specific for α-Syn may be enriched. Subsequently, the mRNA may be reverse-transcribed into cDNA, e.g. by oligo-dT priming. The cDNA may be used as substrate for PCR. These PCRs may generate fragments of the variable domains of heavy and light chains from various B-cells, thus yielding a mixture of information on these molecules from different cells.

To be able to generate information on single HC/LC molecules, the PCR products may then be inserted into plasmids and transformed into bacterial cells. Colony-PCR products of the right size may be sequenced and the nucleotide information may be translated into the required amino acid information. Methods for insertion of PCR products into suitable plasmids, transformation of bacterial cells, isolation of plasmids therefrom, and performing colony PCR as well as sequencing reactions are well known in the art.

The antibodies of the invention may be of various immunoglobulin (Ig) types, for example of the IgA-, IgD-, IgE-, IgG- or IgM-type, preferably of the IgG- or IgM-type including, but not limited to the IgG1-, IgG2-, IgG3-, IgG4-, IgM1- and IgM2-type. In one preferred embodiment, the antibody is of the IgG1-type.

The term "antibody" particularly refers to molecules comprising at least one immunoglobulin heavy chain and at least one immunoglobulin light chain. Each heavy and light chain may comprise a variable and a constant domain. The antigen-binding site may be formed from the variable domains of a heavy and a light chain. A variable region (also referred to as variable domain) comprises complementarity determining regions (CDRs), e.g. a CDR1, a CDR2 and a CDR3 region, and framework regions (FRs) flanking the CDRs. The term "complementarity determining region" is readily understood by the skilled person (see, for example, Harlow and Lane (eds.), Antibodies: A Laboratory Manual, CSHL Press, Cold Spring Harbor, N.Y., 1988; incorporated herein by reference in its entirety) and refers to the stretches of amino acids within the variable domain of an antibody that primarily make contact with the antigen and determine antibody specificity. This region is also known as the hypervariable region.

The invention also encompasses fragments of human antibodies, e.g. portions of the above-mentioned antibodies which comprise at least one antigen-binding site. Examples of antibody fragments include Fab fragments, Fab' fragments, $F(ab')_2$ fragments, Fv fragments, diabodies or single chain antibody molecules and other fragments as long as they exhibit the desired capability of binding to α-Syn.

The term "bind" or "binding" of an antibody means an at least temporary interaction or association with or to a target antigen, e.g. α-Syn, comprising fragments thereof containing an epitope.

Preferably, the antibody or the fragment of the invention binds to an epitope on α-Syn, which is located between amino acid residues 60 and 100 or between amino acid residues 60 and 95 of human α-Syn (SWISS Prot: P37840/SEQ ID NO:1). More preferably, the antibody binds to an epitope between amino acids 73-82 and/or 91-100 of human α-Syn. Most preferably, the epitope bound by the antibody or fragment according to the invention is located between amino acids 74-79 and/or 92-97, of human α-Syn.

The antibodies of the present invention may bind to monomeric α-Syn, to aggregated α-Syn or preferably to both of monomeric and aggregated, e.g. di-, tri- or tetrameric α-Syn. The antibody may also react with oligomeric, particularly tetrameric β-Syn and/or γ-Syn aggregates.

In certain embodiments of the present invention, the antibody may comprise specific heavy chain complementarity determining regions CDR1, CDR2, and/or CDR3 as described below.

Accordingly, in one embodiment, the α-Syn antibody comprises a heavy chain (HC) complementarity determining region 1 (CDR1) having the consensus sequence $GFTX^1SX^2X^3X^4X^5X^6$ (SEQ ID NO.: 27). Within this consensus sequence, $X^1$ may be F or V, $X^2$ may be D or S, $X^3$ may be A, N, or Y, $X^4$ may be A, G, W, or Y, $X^5$ may be I or M, and $X^6$ may be H, N, or S. Preferably, the HC CDR1 has the sequence as shown in any one of SEQ ID NOs.: 28, 29, 30, 31, 32, 33, and 34.

In a further embodiment, the antibody comprises a heavy chain complementarity determining region 2 (CDR2) having the sequence as shown in any one of SEQ ID NOs.: 35, 36, 37, 38, 39, 40, 41, 42, and 43.

In yet a further embodiment, the antibody comprises a heavy chain complementarity determining region 3 (CDR3) having the sequence as shown in any one of SEQ ID NOs.: 44, 45, 46, 47, 48, 49, 50, 51, 52, 53, 54, 55, 56, 57, 58, 59, 60, 61, 62, 63, and 64.

In yet a further embodiment, the antibody comprises a heavy chain complementarity determining region 1 (CDR1) having the consensus sequence GGSISSGGYXWS (SEQ ID NO.: 65). Within this consensus sequence, X may be S or Y. Preferably, the HC CDR1 has the sequence as shown in any one of SEQ ID NOs.: 66 and 67.

In yet a further embodiment, the antibody comprises a heavy chain complementarity determining region 2 (CDR2) having the consensus sequence YIYXSGSTYYNPSLKS (SEQ ID NO.: 68). Within this consensus sequence, X may be H or Y. Preferably, the HC CDR2 has the sequence as shown in any one of SEQ ID NOs.: 69 or 70.

In yet a further embodiment, the antibody comprises a heavy chain complementarity determining region 3 (CDR3) having the sequence as shown in any one of SEQ ID NOs.: 71, 72, 73, 74, and 75.

In yet a further embodiment, the antibody comprises a heavy chain complementarity determining region 1 (CDR1) having the sequence as shown in any one of SEQ ID NOs.: 76, 77, 78, 79, and 80.

In yet a further embodiment, the antibody comprises a heavy chain complementarity determining region 2 (CDR2) having the consensus sequence $X^1IX^2PX^3X^4GX^5X^6X^7YAQKFQG$ (SEQ ID NO.: 81). Within this consensus sequence, $X^1$ may be G, I, or W, $X^2$ may be I, N, or T, $X^3$ may be I, N, or S, $X^4$ may be F, G, H, or S, $X^5$ may be A, G, S or T, $X^6$ may be A or T, and $X^7$ may be N or S. Preferably, the HC CDR2 has the sequence as shown in any one of SEQ ID NOs.: 82, 83, 84, and 85.

In yet a further embodiment, the antibody comprises a heavy chain complementarity determining region 3 (CDR3) having the sequence as shown in any one of SEQ ID NOs.: 86, 87, 88, 89, 90, and 91.

The antibody according to the invention may also comprise specific light chain (LC) complementarity determining regions CDR1, CDR2, and/or CDR3.

Accordingly, in one embodiment, the antibody comprises a light chain complementarity determining region 1 (CDR1) having the sequence as shown in SEQ ID NO.: 92.

In a further embodiment, the antibody comprises a light chain complementarity determining region 2 (CDR2) having the sequence as shown in SEQ ID NO.: 93.

In yet a further embodiment, the antibody comprises a light chain complementarity determining region 3 (CDR3) having the consensus sequence $MQALQX^1X^2X^3T$ (SEQ ID NO.: 94). Within this consensus sequence, $X^1$ may not be present or may be T, $X^2$ may be F or P, and $X^3$ may be R, W, or Y. Preferably, the LC CDR3 has the sequence as shown in any one of SEQ ID NOs.: 95, 96, 97, and 98.

In yet a further embodiment, the antibody comprises a light chain complementarity determining region 1 (CDR1) having the consensus sequence $RASQSVSSX^1X^2LA$ (SEQ ID NO.: 99). Within this consensus sequence, $X^1$ may not be present or may be S, and $X^2$ may be N or Y. Preferably, the LC CDR1 has the sequence as shown in any one of SEQ ID NOs.: 100, 101, and 102.

In yet a further embodiment, the antibody comprises a light chain complementarity determining region 2 (CDR2) having the consensus sequence $X^1ASX^2RAT$ (SEQ ID NO.: 103). Within this consensus sequence, $X^1$ may be D or G, and $X^2$ may be N, S, or T. Preferably, the LC CDR2 has the sequence as shown in any one of SEQ ID NOs.: 104, 105, 106.

In yet a further embodiment, the antibody comprises a light chain complementarity determining region 3 (CDR3) having the sequence as shown in any one of SEQ ID NOs.: 107, 108, 109, 110, 111, 112, 113, 114, 145, 146, and 147.

In yet a further embodiment, the antibody comprises a light chain complementarity determining region 1 (CDR1) having the consensus sequence $RX^1SQX^2IX^3X^4X^5X^6$ (SEQ ID NO.: 115).

Within this consensus sequence, $X^1$ may be A or M, $X^2$ may be G or S, $X^3$ may be R or S, $X^4$ may be N or S, $X^5$ may be D, W, or Y, and $X^6$ may be A or G. Preferably, the LC CDR1 has the sequence as shown in any one of SEQ ID NOs.: 116, 117, 118, 119, 120, 121, and 122.

In yet a further embodiment, the antibody comprises a light chain complementarity determining region 2 (CDR2) having the sequence as shown in any one of SEQ ID NOs.: 123, 124, 125, 126, and 127.

In yet a further embodiment, the antibody comprises a light chain complementarity determining region 3 (CDR3) having the sequence as shown in any one of SEQ ID NOs.: 128, 129, 130, 131, 132, 133, 134, 135, 136, 137, 138, 139, 140, 141, 142, 143 and 144.

The antibody of the present invention may preferably comprise a specific combination of CDRs (i.e. of CDR1, CDR2, and CDR3) within one heavy chain.

Accordingly, in one preferred embodiment, the antibody comprises a heavy chain comprising complementarity determining regions CDR1, CDR2, and CDR3, wherein CDR1 is selected from the sequences shown in SEQ ID NOs.: 28, 29, 30, 31, 32, 33, and 34, CDR2 is selected from the sequences shown in SEQ ID NOs.: 35, 36, 37, 38, 39, 40, 41, 42, and 43, and CDR3 is selected from the sequences shown in SEQ ID NOs.: 44, 45, 46, 47, 48, 49, 50, 51, 52, 53, 54, 55, 56, 57, 58, 59, 60, 61, 62, 63, and 64.

In a further preferred embodiment, the HC CDR1 is selected from the sequences shown in SEQ ID NOs.: 66 and 67, HC CDR2 is selected from the sequences shown in SEQ ID NOs.: 69 and 70, and HC CDR3 is selected from the sequences shown in SEQ ID NOs.: 71, 72, 73, 74, and 75.

In a further preferred embodiment, the HC CDR1 is selected from the sequences shown in SEQ ID NOs.: 76, 77, 78, 79, and 80, HC CDR2 is selected from the sequences shown in SEQ ID NOs.: 82, 83, 84, and 85, and HC CDR3 is selected from the sequences shown in SEQ ID NOs.: 86, 87, 88, 89, 90, and 91.

Most preferably, the antibody of the invention comprises a heavy chain comprising three CDRs, wherein the combination of CDR1, CDR2, and CDR3 is selected from those shown in Table 1, Table 2 and Table 3. It is understood that each line of each of these Tables represents one specific combination of a CDR1, a CDR2, and a CDR3.

TABLE 1

Specific CDR combinations

| CDR1 | CDR2 | CDR3 |
|---|---|---|
| GFTFSSYGMH (SEQ ID NO: 32) | VIWYDGSNKYYADSVKG (SEQ ID NO: 39) | DWGIVDTAMVPYYYYYGMDV (SEQ ID NO: 50) |
| GFTFSSYGMH (SEQ ID NO: 32) | VIWYDGSNKYYADSVKG (SEQ ID NO: 39) | DRRGIAATAGYYYGMDV (SEQ ID NO: 49) |
| GFTFSSYGMH (SEQ ID NO: 32) | VIWYDGSNKYYADSVKG (SEQ ID NO: 39) | DRGFGYCSSTSCHTEDAFDI (SEQ ID NO: 47) |
| GFTFSSYGMH (SEQ ID NO: 32) | VISYDGSNKYYADSVKG (SEQ ID NO: 40) | ERYYYMDV (SEQ ID NO: 53) |
| GFTFSSYGMH (SEQ ID NO: 32) | VISYDGSNKYYADSVKG (SEQ ID NO: 40) | QDIAAAAPYYFDY (SEQ ID NO: 60) |

TABLE 1-continued

Specific CDR combinations

| CDR1 | CDR2 | CDR3 |
|---|---|---|
| GFTFSSYGMH (SEQ ID NO: 32) | VISYDGSNKYYADSVKG (SEQ ID NO: 40) | AMVRGVTKPFDY (SEQ ID NO: 44) |
| GFTFSSYGMH (SEQ ID NO: 32) | VISYDGSNKYYADSVKG (SEQ ID NO: 40) | GGDYYDSSGYYLPWY (SEQ ID NO: 54) |
| GFTFSSYGMH (SEQ ID NO: 32) | VISYDGSNKYYADSVKG (SEQ ID NO: 40) | DLVDYDSSGYYPDY (SEQ ID NO: 46) |
| GFTFSSYGMH (SEQ ID NO: 32) | AISGSGGSTYYADSVKG (SEQ ID NO: 35) | AYYYYDSSGYGY (SEQ ID NO: 45) |
| GFTFSSYAMH (SEQ ID NO: 30) | VISYDGSNKYYADSVKG (SEQ ID NO: 40) | EAPSSGWYPYYYYMDV (SEQ ID NO: 51) |
| GFTFSSYAMH (SEQ ID NO: 30) | VISYDGSNKYYADSVKG (SEQ ID NO: 40) | YCSSTSCSSEYFGH (SEQ ID NO: 63) |
| GFTFSSYAMH (SEQ ID NO: 30) | VISYDGSNKYYADSVKG (SEQ ID NO: 40) | GVVPAAESWFDP (SEQ ID NO: 57) |
| GFTFSSYAMH (SEQ ID NO: 30) | VISYDGSNKYYADSVKG (SEQ ID NO: 40) | QDIAAAAPYYFDY (SEQ ID NO: 60) |
| GFTFSSYAMH (SEQ ID NO: 30) | VISYDGSNKYYADSVKG (SEQ ID NO: 40) | YYYDSSAVEGDAFDI (SEQ ID NO: 64) |
| GFTFSSYAMS (SEQ ID NO: 31) | AISGSGGSTYYADSVKG (SEQ ID NO: 35) | DWGIVDTAMVPYYYYGMDV (SEQ ID NO: 50) |
| GFTFSSYAMS (SEQ ID NO: 31) | AISGSGGSTYYADSVKG (SEQ ID NO: 35) | DRRGIAATAGYYYGMDV (SEQ ID NO: 49) |
| GFTFSSYAMS (SEQ ID NO: 31) | AISGSGGSTYYADSVKG (SEQ ID NO: 35) | DRHPGYCSSTSCFVRYFDY (SEQ ID NO: 48) |
| GFTFSSYAMS (SEQ ID NO: 31) | AISGSGGSTYYADSVKG (SEQ ID NO: 35) | GGDYYDSSGYYLPWY (SEQ ID NO: 54) |
| GFTFSSYAMS (SEQ ID NO: 31) | AISGSGGSTYYADSVKG (SEQ ID NO: 35) | KTYYYYDSSGYGY (SEQ ID NO: 59) |
| GFTFSSYAMS (SEQ ID NO: 31) | AISGSGGSTYYADSVKG (SEQ ID NO: 35) | QDIAAAAPYYFDY (SEQ ID NO: 60) |
| GFTFSSYAMS (SEQ ID NO: 31) | AISGSGGSTYYADSVKG (SEQ ID NO: 35) | SGASLRAFDI (SEQ ID NO: 61) |
| GFTFSSYAMS (SEQ ID NO: 31) | AISGSGGSTYYADSVKG (SEQ ID NO: 35) | SGYYYPLDY (SEQ ID NO: 62) |
| GFTFSSYWMS (SEQ ID NO: 33) | NIKQDGSEKYYVDSVKG (SEQ ID NO: 37) | EHRGGYYDILTGYTKHGGSNDY (SEQ ID NO: 52) |
| GFTFSSYWMS (SEQ ID NO: 33) | NIKQDGSEKYYVDSVKG (SEQ ID NO: 37) | DLVDYDSSGYYPDY (SEQ ID NO: 46) |
| GFTFSSYWMS (SEQ ID NO: 33) | NIKQDGSEKYYVDSVKG (SEQ ID NO: 37) | GTDTESVAAPYYYYMDV (SEQ ID NO: 55) |
| GFTFSSYWMS (SEQ ID NO: 33) | NIKQDGSEKYYADSVKG (SEQ ID NO: 36) | ERYYYMDV (SEQ ID NO: 53) |
| GFTFSDYYMS (SEQ ID NO: 29) | YISSSGGTIYYADSVKG (SEQ ID NO: 42) | GVAGRFDY (SEQ ID NO: 56) |
| GFTFSDYYMS (SEQ ID NO: 29) | YISSSSSYTNYADSVKG (SEQ ID NO: 43) | YYYDSSAVEGDAFDI (SEQ ID NO: 64) |
| GFTFSDAWIN (SEQ ID NO: 28) | RIKSKTDGGTTDYAAPVKG (SEQ ID NO: 38) | KDGSGSYYHYYYYVMDV (SEQ ID NO: 58) |
| GFTVSSNYMS (SEQ ID NO: 34) | VIYSGGSTYYADSVKG (SEQ ID NO: 41) | SGASLRAFDI (SEQ ID NO: 61) |

TABLE 2

| Specific CDR combinations | | |
|---|---|---|
| CDR1 | CDR2 | CDR3 |
| GGSISSGGYSWS (SEQ ID NO: 66) | YIYHSGSTYYNPSLKS (SEQ ID NO: 69) | GTEYCTNGACYMGYYYYYMDV (SEQ ID NO: 74) |
| GGSISSGGYSWS (SEQ ID NO: 66) | YIYHSGSTYYNPSLKS (SEQ ID NO: 69) | GTEYCTNGVCYMGYYYYYMDV (SEQ ID NO: 75) |
| GGSISSGGYSWS (SEQ ID NO: 66) | YIYHSGSTYYNPSLKS (SEQ ID NO: 69) | AGYYYYYMDV (SEQ ID NO: 71) |
| GGSISSGGYSWS (SEQ ID NO: 66) | YIYHSGSTYYNPSLKS (SEQ ID NO: 69) | AHPVRGSGSYYNRNYYYYYMDV (SEQ ID NO: 72) |
| GGSISSGGYYWS (SEQ ID NO: 67) | YIYYSGSTYYNPSLKS (SEQ ID NO: 70) | GSREGYGDRIDY (SEQ ID NO: 73) |
| GGSISSGGYYWS (SEQ ID NO: 67) | YIYYSGSTYYNPSLKS (SEQ ID NO: 70) | GTEYCTNGVCYMGYYYYYMDV (SEQ ID NO: 75) |

TABLE 3

| Specific CDR combinations | | |
|---|---|---|
| CDR1 | CDR2 | CDR3 |
| GYTFTGYYMH (SEQ ID NO: 79) | WINPNSGGTNYAQKFQG (SEQ ID NO: 85) | DSGSSGWYVPYWYFDL (SEQ ID NO: 88) |
| GYTFTGYYMH (SEQ ID NO: 79) | WINPNSGGTNYAQKFQG (SEQ ID NO: 85) | PIGGGPSGWYETSCFDP (SEQ ID NO: 89) |
| GYTFTGYYMH (SEQ ID NO: 79) | WINPNSGGTNYAQKFQG (SEQ ID NO: 85) | AKDYDFWRGSTGMRYLDV (SEQ ID NO: 86) |
| GYTFTGYYMH (SEQ ID NO: 79) | WINPNSGGTNYAQKFQG (SEQ ID NO: 85) | DKRCSSTSCQPYYYYYMDV (SEQ ID NO: 87) |
| GYTFTGYYMH (SEQ ID NO: 79) | WINPNSGGTNYAQKFQG (SEQ ID NO: 85) | TSYGDSSSSSYYYYYGMDV (SEQ ID NO: 90) |
| GYTFTSYYMH (SEQ ID NO: 80) | IINPSGGSTSYAQKFQG (SEQ ID NO: 83) | DSGSSGWYVPYWYFDL (SEQ ID NO: 88) |
| GYIITNYYIH (SEQ ID NO: 78) | IITPSHGATNYAQKFQG (SEQ ID NO: 84) | AKDYDFWRGSTGMRYLDV (SEQ ID NO: 86) |
| GYIIANYYIH (SEQ ID NO: 77) | IITPSHGATNYAQKFQG (SEQ ID NO: 84) | AKDYDFWRGSTGMRYLDV (SEQ ID NO: 86) |
| GGTFSSYAIS (SEQ ID NO: 76) | GIIPIFGTANYAQKFQG (SEQ ID NO: 82) | VDYSNYVVDY (SEQ ID NO: 91) |

According to the present invention, it is further preferred that the antibody comprises a specific combination of CDRs (i.e. of CDR1, CDR2, and CDR3) within one light chain.

Thus, in one preferred embodiment, the antibody comprises a light chain comprising complementarity determining regions CDR1, CDR2, and CDR3, wherein LC CDR1 has the sequence shown in SEQ ID NO.: 92, LC CDR2 has the sequence shown in SEQ ID NO.: 93, and LC CDR3 is selected from the sequences shown in SEQ ID NOs.: 95, 96, 97, and 98.

In a further preferred embodiment, the LC CDR1 is selected from the sequences shown in SEQ ID NOs.: 100, 101, and 102, LC CDR2 is selected from the sequences shown in SEQ ID NOs.: 104, 105, and 106, and LC CDR3 is selected from the sequences shown in SEQ ID NOs.: 107, 108, 109, 110, 111, 112, 113, 114, 145, 146, and 147.

In a further preferred embodiment, the LC CDR1 is selected from the sequences shown in SEQ ID NOs.: 116, 117, 118, 119, 120, 121, and 122, LC CDR2 is selected from the sequences shown in SEQ ID NOs.: 123, 124, 125, 126, and 127, and LC CDR3 is selected from the sequences shown in SEQ ID NOs.: 128, 129, 130, 131, 132, 133, 134, 135, 136, 137, 138, 139, 140, 141, 142, 143, and 144.

Most preferably, the antibody of the invention comprises a light chain comprising three CDRs, wherein the combination of CDR1, CDR2, and CDR3 is selected from those shown in Table 4, Table 5 and Table 6. It is understood that each line of each of these Tables represents one specific combination of a CDR1, a CDR2, and a CDR3.

TABLE 4

| Specific CDR combinations | | |
|---|---|---|
| CDR1 | CDR2 | CDR3 |
| RSSQSLLHSNGYNYLD (SEQ ID NO: 92) | LGSNRAS (SEQ ID NO: 93) | MQALQTPYT (SEQ ID NO: 97) |
| RSSQSLLHSNGYNYLD (SEQ ID NO: 92) | LGSNRAS (SEQ ID NO: 93) | MQALQTPWT (SEQ ID NO: 96) |
| RSSQSLLHSNGYNYLD (SEQ ID NO: 92) | LGSNRAS (SEQ ID NO: 93) | MQALQTPRT (SEQ ID NO: 95) |
| RSSQSLLHSNGYNYLD (SEQ ID NO: 92) | LGSNRAS (SEQ ID NO: 93) | MQATQFRT (SEQ ID NO: 98) |

TABLE 5

| Specific CDR combinations | | |
|---|---|---|
| CDR1 | CDR2 | CDR3 |
| RASQSVSSSYLA (SEQ ID NO: 101) | GASSRAT (SEQ ID NO: 105) | QQYGSSWT (SEQ ID NO: 109) |
| RASQSVSSYLA (SEQ ID NO: 102) | DASNRAT (SEQ ID NO: 104) | QQRSNWPPYT (SEQ ID NO: 108) |
| RASQSVSSYLA (SEQ ID NO: 102) | DASNRAT (SEQ ID NO: 104) | QQRSNWPPT (SEQ ID NO: 107) |
| RASQSVSSNLA (SEQ ID NO: 100) | GASTRAT (SEQ ID NO: 106) | QQYNNWYT (SEQ ID NO: 114) |
| RASQSVSSNLA (SEQ ID NO: 100) | GASTRAT (SEQ ID NO: 106) | QQYNNWWT (SEQ ID NO: 113) |
| RASQSVSSNLA (SEQ ID NO: 100) | GASTRAT (SEQ ID NO: 106) | QQYNNWPRT (SEQ ID NO: 112) |
| RASQSVSSNLA (SEQ ID NO: 100) | GASTRAT (SEQ ID NO: 106) | QQYNNWPLT (SEQ ID NO: 110) |
| RASQSVSSNLA (SEQ ID NO: 100) | GASTRAT (SEQ ID NO: 106) | QQYNNWPPMYT (SEQ ID NO: 111) |
| RASQSVSSNLA (SEQ ID NO: 100) | GASTRAT (SEQ ID NO: 106) | QQYGSSPRT (SEQ ID NO: 147) |
| RASQSVSSNLA (SEQ ID NO: 100) | GASTRAT (SEQ ID NO: 106) | QQRSNWPPYT (SEQ ID NO: 108) |

TABLE 6

| Specific CDR combinations | | |
|---|---|---|
| CDR1 | CDR2 | CDR3 |
| RASQGISNYLA (SEQ ID NO: 117) | AASSLQS (SEQ ID NO: 123) | QQYNSYPVT (SEQ ID NO: 137) |
| RASQGISNYLA (SEQ ID NO: 117) | AASSLQS (SEQ ID NO: 123) | QQYNSYPYT (SEQ ID NO: 139) |
| RASQGISNYLA (SEQ ID NO: 117) | AASSLQS (SEQ ID NO: 123) | QQYNSYPWT (SEQ ID NO: 138) |
| RASQGISNYLA (SEQ ID NO: 117) | AASSLQS (SEQ ID NO: 123) | LQHNSYPFT (SEQ ID NO: 131) |
| RASQGISNYLA (SEQ ID NO: 117) | AASSLQS (SEQ ID NO: 123) | LQHNSYPVT (SEQ ID NO: 132) |

TABLE 6-continued

| Specific CDR combinations | | |
|---|---|---|
| CDR1 | CDR2 | CDR3 |
| RASQGISSYLA (SEQ ID NO: 119) | AASTLQS (SEQ ID NO: 124) | QQLNSYPLFT (SEQ ID NO: 135) |
| RASQGISSWLA (SEQ ID NO: 118) | AASSLQS (SEQ ID NO: 123) | LQDYNYPYT (SEQ ID NO: 130) |
| RASQGISSWLA (SEQ ID NO: 118) | AASSLQS (SEQ ID NO: 123) | QQANSFPIT (SEQ ID NO: 133) |
| RASQGISSWLA (SEQ ID NO: 118) | AASSLQS (SEQ ID NO: 123) | QQYNSYPVT (SEQ ID NO: 137) |
| RMSQGISSWLA (SEQ ID NO: 121) | AASSLQS (SEQ ID NO: 124) | QQANSFPLT (SEQ ID NO: 134) |
| RMSQGISSYLA (SEQ ID NO: 122) | AASSLQS (SEQ ID NO: 124) | QQANSFPLT (SEQ ID NO: 134) |
| RASQSISSWLA (SEQ ID NO: 120) | KASSLES (SEQ ID NO: 127) | QQYNSYSRKYT (SEQ ID NO: 140) |
| RASQGIRNDLG (SEQ ID NO: 116) | AASSLQS (SEQ ID NO: 123) | LGDYNYPYT (SEQ ID NO: 128) |
| RASQGIRNDLG (SEQ ID NO: 116) | AASSLQS (SEQ ID NO: 123) | LQHNSYPFT (SEQ ID NO: 131) |
| RASQGIRNDLG (SEQ ID NO: 116) | AASTLVS (SEQ ID NO: 125) | LQDNNYPRT (SEQ ID NO: 129) |
| RASQGIRNDLG (SEQ ID NO: 116) | DASNLET (SEQ ID NO: 126) | QQYDNLPPFT (SEQ ID NO: 136) |

As described above, the complementarity determining regions (CDRs) of an antibody may be flanked by framework regions (FRs). A heavy or light chain of an antibody containing three CDRs contains e.g. four FRs.

In one embodiment, CDRs 1, 2, and 3 of the heavy chain of an inventive antibody are flanked by four FRs consisting of a consensus sequence as shown in SEQ ID NOs.: 3, 4, 5, and 6. An antibody chain containing these FRs is sometimes referred to herein as $HC_v$ Type 1. According to the invention, the HC CDRs may also be flanked by four FRs consisting of a consensus sequence as shown in SEQ ID NOs.: 7, 8, 9, and 10 (sometimes referred to as $HC_v$ Type 2), or, in another embodiment, by four FRs consisting of a consensus sequence as shown in SEQ ID NOs.: 11, 12, 13, and 14 (sometimes referred to as $HC_v$ Type 3).

Similarly, the CDRs of the light chain may be flanked by FRs. In one embodiment, LC CDRs 1, 2 and 3 are flanked by four FRs consisting of a consensus sequence as shown in SEQ ID NOs.: 15, 16, 17, and 18, or, in another embodiment, by four FRs consisting of a consensus sequence as shown in SEQ ID NOs.: 19, 20, 21, and 22. In yet another embodiment, LC CDRs are flanked by four FRs consisting of a consensus sequence as shown in SEQ ID NOs.: 23, 24, 25, and 26.

Variants of these framework regions are also within the scope of the present invention. In particular, FRs may contain amino acid substitutions at specific positions. For example, in $HC_v$ Type 1 FR1(SEQ ID NO.: 3), the amino acid (aa) at position 1 may also be E or G instead of the Q shown in the consensus sequence. Further possible substitutions include those at positions 5 (L instead of V, abbreviated V>L), 10 (G>D), 11 (V>L), 13 (Q>K), 16 (R>G), 19 (R>G), and 23 (A>V) of SEQ ID NO.: 3.

In $HC_v$ Type 1 FR2 (SEQ ID NO.: 4), possible aa substitutions include those at positions 1 (W>R), 2 (V>I), and 14 (A>G/S; i.e. A can be replaced by G or S) of SEQ ID NO.: 4.

In $HC_v$ Type 1 FR3 (SEQ ID NO.: 5), possible aa substitutions include those at positions 8 (N>D), 9 (A>T), 12 (S>A), and 22 (T>S) of SEQ ID NO.: 5.

In $HC_v$ Type 1 FR4 (SEQ ID NO.: 6), possible aa substitutions include those at positions 1 (W>V), 3 (Q>K), 4 (G>E), 6 (T>L/M), 8 (T>N), 25 (S>C), 27(K>R), 31 (G>E), and 32 (G>S) of SEQ ID NO.: 6.

Some amino acid substitutions may be linked, e.g. substitutions at positions 11, 13, and 16 of SEQ ID NO: 3, substitutions at positions 8 and 22 of SEQ ID NO: 5, substitutions at positions 9 and 12 of SEQ ID NO: 5, substitutions at positions 25 and 27 of SEQ ID NO: 6, or substitutions at positions 31 and 32 of SEQ ID NO: 6.

In $HC_v$ Type 2 FR1(SEQ ID NO.: 7), possible aa substitutions include those at positions 2 (L>V), 9 (S>P), and 23 (A>T) of SEQ ID NO.: 7. The substitutions at positions 2 and 9 may be linked.

In $HC_v$ Type 2 FR2 (SEQ ID NO.: 8), e.g. the amino acid at position 6 may be substituted (P>H).

In $HC_v$ Type 2 FR3 (SEQ ID NO.: 9), possible aa substitutions include those at positions 8 (R>T) and 16 (K>R) of SEQ ID NO.: 9.

In $HC_v$ Type 2 FR4 (SEQ ID NO.: 10), possible aa substitutions include those at positions 3 (K>Q), 6 (T>L), 25 (S>C) and 27 (K>R) of SEQ ID NO.: 10. The substitutions at positions 3, 6 and 25 may be linked.

In $HC_v$ Type 3 FR1(SEQ ID NO.: 11), e.g. the amino acid at position 16 may be substituted (A>S).

In $HC_v$ Type 3 FR3 (SEQ ID NO.: 13), possible aa substitutions include those at positions 1 (W>R), 4 (M>I), 6 (R>A), 8 (T>E), 10 (I>T), 13 (A>V), 16 (E>H), 19 (R>S), 23 (D>E) and 32 (R>T) of SEQ ID NO.: 13. The substitutions at positions 6, 8, 10, 19, and 23, or substitutions at positions 6, 10, 13, 16, 19, and 23 may be linked.

In $HC_v$ Type 3 FR4 (SEQ ID NO.: 14), possible aa substitutions include those at positions 3 (R>P/K/Q), 6 (L>T), 25 (C>S), 27 (R>K), 29 (T>A), 31 (E>G), 32 (S>G), 48 (V>G), 49 (T>R), and 50 (V>G) of SEQ ID NO.: 14. The substitutions at positions 31 and 32, or substitutions at positions 48 and 49 may be linked.

In $LC_v$ Type 1 FR1(SEQ ID NO.: 15), e.g. the amino acid at position 7 may be substituted (S>T).

In $LC_v$ Type 1 FR3 (SEQ ID NO.: 17), e.g. the amino acid at position 20 may be substituted (S>G).

In $LC_v$ Type 1 FR4 (SEQ ID NO.: 18), possible aa substitutions include those at positions 6 (K>R), 7 (L>V), 9 (I>S) and 14 (A>T) of SEQ ID NO.: 18.

In $LC_v$ Type 2 FR1(SEQ ID NO.: 19), possible aa substitutions include those at positions 1 (E>K), 4 (L>M), 9 (G>A), 13 (L>V) and 22 (S>P) of SEQ ID NO.: 19. The substitutions at positions 4 and 13 may be linked.

In $LC_v$ Type 2 FR3 (SEQ ID NO.: 21), possible aa substitutions include those at positions 4 (D>A), 14 (D>E), 18 (T>I), 21 (R>S), 23 (E>Q), 24 (P>S), and 25 (E>K) of SEQ ID NO.: 21. The substitutions at positions 23 and 24 may be linked.

In $LC_v$ Type 2 FR4 (SEQ ID NO.: 22), possible aa substitutions include those at positions 3 (Q>G), 6 (K>R), and 7 (V>L) of SEQ ID NO.:22. The substitutions at positions 6 and 7 may be linked.

In $LC_v$ Type 3 FR1(SEQ ID NO.: 23), possible aa substitutions include those at positions 1 (D>A/V), 3 (Q>W), 5 (T>A), 10 (S>T/L), 11 (L>V), and 22 (T>S) of SEQ ID NO.: 23.

In $LC_v$ Type 3 FR2 (SEQ ID NO.: 24), possible aa substitutions include those at positions 2 (F>Y), 5 (K>R), 7 (G>R), and 12 (S>L/R) of SEQ ID NO.: 24.

In $LC_v$ Type 3 FR3 (SEQ ID NO.: 25), possible aa substitutions include those at positions 5 (K>R), 14 (D>E), 17 (L>F), 20 (S>T), 21 (S>T), 25 (E>D), 27 (F>I/S), and 29 (T>N) of SEQ ID NO.: 25. The substitutions at positions 20 and 21 may be linked.

In $LC_v$ Type 3 FR4 (SEQ ID NO.: 26), possible aa substitutions include those at positions 3 (Q>P), 7 (L>V), and 8 (E>D) of SEQ ID NO.: 26.

Preferably, the framework regions of either the heavy or the light chain show a maximum exchange of two amino acids, one amino acid, or are identical to the consensus sequence.

It is particularly preferred that the antibody of the invention comprises a heavy chain comprising a specific combination of framework regions and complementarity determining regions.

Thus, in one embodiment of the invention, said antibody heavy chain comprises FRs consisting of a consensus sequence as shown in SEQ ID NOs.: 3, 4, 5, and 6 (i.e. 3-6) or variants thereof, and further comprises complementarity determining regions CDR1, CDR2, and CDR3, wherein CDR1 is selected from the sequences shown in SEQ ID NOs.: 28, 29, 30, 31, 32, 32, 33, and 34 (28-34), CDR2 is selected from the sequences shown in SEQ ID NOs.: 35, 36, 37, 38, 39, 40, 41, 42, and 43 (35-43), and CDR3 is selected from the sequences shown in SEQ ID NOs.: 44, 45, 46, 47, 48, 49, 50, 51, 52, 53, 54, 55, 56, 57, 58, 59, 60, 61, 62, 63, and 64 (44-64).

In another embodiment, said antibody heavy chain comprises FRs consisting of a consensus sequence as shown in SEQ ID NOs.: 7, 8, 9, and 10 (7-10) or variants thereof, and further comprises complementarity determining regions CDR1, CDR2, and CDR3, wherein CDR1 is selected from the sequences shown in SEQ ID NOs.: 66 and 67, CDR2 is selected from the sequences shown in SEQ ID NOs.: 69 and 70, and CDR3 is selected from the sequences shown in SEQ ID NOs.: 71, 72, 73, 74, and 75 (71-75).

In yet another embodiment, said antibody heavy chain comprises FRs consisting of a consensus sequence as shown in SEQ ID NOs.: 11, 12, 13, and 14 (11-14) or variants thereof, and further comprises complementarity determining regions CDR1, CDR2, and CDR3, wherein CDR1 is selected from the sequences shown in SEQ ID NOs.: 76, 77, 78, 79, and 80 (76-80), CDR2 is selected from the sequences shown in SEQ ID NOs.: 82, 83, 84, and 85 (82-85), and CDR3 is selected from the sequences shown in SEQ ID NOs.: 86, 87, 88, 89, 90, and 91 (86-91).

In a most preferred embodiment, the antibody heavy chain comprises FRs consisting of a consensus sequence comprising SEQ ID NOs.: 3, 4, 5, and 6 or variants thereof as defined supra, and further comprises a specific combination of CDR1, CDR2, and CDR3 as shown in Table 1, where each line of the Table represents one specific CDR1, 2, 3 combination.

In a further most preferred embodiment, the antibody heavy chain comprises FRs consisting of a consensus sequence comprising SEQ ID NOs.: 7, 8, 9, and 10 or variants thereof as defined supra, and further comprises a specific combination of CDR1, CDR2, and CDR3 as shown in Table 2.

In yet a further most preferred embodiment, the antibody heavy chain comprises FRs consisting of a consensus sequence comprising SEQ ID NOs.: 11, 12, 13, and 14 or variants thereof as defined supra, and further comprises a specific combination of CDR1, CDR2, and CDR3 as shown in Table 3.

Likewise, it is particularly preferred that the antibody of the invention comprises a light chain comprising a specific combination of FRs and CDRs. Accordingly, in one embodiment of the invention, said antibody light chain comprises FRs consisting of a consensus sequence comprising SEQ ID NOs.: 15, 16, 17, and 18 (15-18) or variants thereof, and further comprises complementarity determining regions CDR1, CDR2, and CDR3, wherein CDR1 has the sequence shown in SEQ ID NO.: 92, CDR2 has the sequence shown in SEQ ID NO.: 93, and CDR3 is selected from the sequences shown in SEQ ID NOs.: 95, 96, 97, and 98 (95-98).

In another embodiment, said antibody light chain comprises FRs consisting of a consensus sequence comprising SEQ ID NOs.: 19, 20, 21, and 22, or variants thereof, and further comprises complementarity determining regions CDR1, CDR2, and CDR3, wherein CDR1 is selected from the sequences shown in SEQ ID NOs.: 100, 101, and 102, CDR2 is selected from the sequences shown in SEQ ID NOs.: 104, 105, and 106, and CDR3 is selected from the sequences shown in SEQ ID NOs.: 107, 108, 109, 110, 111, 112, 113, 114, 145, 146, and 147.

In another embodiment, said antibody light chain comprises FRs consisting of a consensus sequence comprising SEQ ID NOs.: 23, 24, 25, and 26 or variants thereof, and further comprises complementarity determining regions CDR1, CDR2, and CDR3, wherein CDR1 is selected from the sequences shown in SEQ ID NOs.: 116, 117, 118, 119, 120, 121, and 122, CDR2 is selected from the sequences shown in SEQ ID NOs.: 123, 124, 125, 126, and 127, and CDR3 is selected from the sequences shown in SEQ ID NOs.: 128, 129, 130, 131, 132, 133, 134, 135, 136, 137, 138, 139, 140, 141, 142, 143, and 144.

In a most preferred embodiment, the antibody light chain comprises FRs consisting of a consensus sequence comprising SEQ ID NOs.: 15, 16, 17, and 18 or variants thereof as defined supra, and further comprises a specific combination of CDR1, CDR2, and CDR3 as shown in Table 4, where each line of the Table represents one specific CDR1, 2, 3 combination.

In a further most preferred embodiment, the antibody light chain comprises FRs consisting of a consensus sequence comprising SEQ ID NOs.: 19, 20, 21, and 22 or variants thereof as defined supra, and further comprises a specific combination of CDR1, CDR2, and CDR3 as shown in Table 5.

In yet a further most preferred embodiment, the antibody light chain comprises FRs consisting of a consensus sequence as shown in SEQ ID NOs.: 23, 24, 25, and 26 or variants thereof as defined supra, and further comprises a specific combination of CDR1, CDR2, and CDR3 as shown in Table 6.

In a further preferred embodiment, the antibody of the present invention is characterized by a light chain sequence (SEQ ID NO:2) or a variant thereof:

```
  1 EIVLTQSPAT LSLSPGERAT LSCRASQSVS SSYLAWYQQK PGQAPRLLIY
 51 GASSRATGIP DRFSGSGSGT DFTLTISSLQ SEDFATYYCR LTEEKGWMYL
101 GYTFGQGTKL EIKRTVAAPS VFIFPPSDEQ LKSGTASVVC LLNNFYPREA
151 KVQWKVDNAL QSGNSQESVT EQDSKDSTYS LSSTLTLSKA DYEKHKVYAC
201 EVTHQGLSSP VTKSFNRGEC
```

The light chain sequence above comprises a constant domain (aa111-220) and a variable domain (aa1-110). The variable domain comprises Framework (FR) and CDR sequences. The CDR sequences are located from aa23-35 (LCDR1), aa51-57 (LCDR2) and aa90-102 (LCDR3).

The term "variant" as used hereinabove, particularly includes amino acid sequences which differ from the indicated sequence by partial or complete deletion of the constant domain and/or by partial or complete exchange of FR sequences. Further, the term "variant" also includes amino acid sequences which differ from the indicated CDR sequences by substitution, deletion or addition of one or two amino acids, preferably by substitution, deletion or addition of one amino acid.

The antibody of the present invention may be coupled to a heterologous group, e.g. an effector group. Such an antibody conjugate is especially suitable for therapeutic applications. The term "effector group" may refer to a cytotoxic group, such as a radioisotope or radionuclide, a toxin, a therapeutic group or another effector group known in the art. Alternatively, the antibody of the invention may be coupled to a labelling group. Such an antibody conjugate is particularly suitable for diagnostic applications. As used herein, the term "labelling group" refers to a detectable marker, e.g. a radiolabelled amino acid or biotinyl moiety, a fluorescent marker, an enzyme or any other type of marker which is known in the art.

The antibody of the present invention is suitable for use in medicine, particularly for use in human medicine. The antibody may be used in the treatment of a neurodegenerative disorder, which deposits α-Syn, for example Parkinson's disease or Dementia with Lewy bodies (DLB). More preferably, the disorder is Parkinson's disease. The treatment may comprise a passive immune therapy thereby reducing and/or inhibiting detrimental effects of α-Syn aggregate formation in the nervous system, particularly in the central nervous system of the subject to be treated. These detrimental effects may include cytotoxicity, particularly neurotoxicity.

Furthermore, the antibody of the invention may be used as a diagnostic agent, for example for the diagnosis of neurodegenerative disorders, such as PD or DLB. More preferably, the antibody of the invention may be used as a diagnostic agent for PD.

The invention also refers to a nucleic acid molecule encoding the antibody as described above. The term "nucleic acid molecule" encompasses DNA, e.g. single- or double-stranded DNA, or RNA. The DNA may be of genomic, cDNA or synthetic origin, or a combination thereof. The nucleic acid molecule of the invention may be in operative linkage to an expression control sequence, i.e. to a sequence which is necessary to effect the expression of coding nucleic acid sequences. Such expression control sequences may include promoters, enhancers, ribosomal binding sites and/or transcription termination sequences. Specific examples of suitable expression control sequences are known in the art.

The nucleic acid molecule of the invention may be located on a vector which may additionally contain a replication origin and/or a selection marker gene. Examples of vectors are e.g. plasmids, cosmids, phages, viruses etc.

Further, the invention refers to a recombinant cell, which comprises the nucleic acid molecule as described above. The nucleic acid molecule may be introduced into the recombinant cell by transformation, transfection or transduction according to any method known in the art. The recombinant cell may e.g. be a prokaryotic or eukaryotic cell. Preferably, the cell is a mammalian cell, e.g. a hamster, rabbit, or human cell. Preferably, the cell is a human cell.

The antibody of the invention may be prepared by a method, wherein the cell as described above is cultured under conditions which allow expression of the antibody encoding nucleic acid molecule. The antibody may be collected from the cultured cell or the culture supernatant. Preferably, the antibody is prepared from a mammalian, particularly from a human cell.

Still a further aspect of the present invention relates to a pharmaceutical composition comprising the antibody, the nucleic acid molecule or the recombinant cell as described above together with a pharmaceutically acceptable carrier. The term "carrier" includes agents, e.g. diluents, stabilizers, adjuvants or other types of excipients that are non-toxic to the cell or mammal to be exposed thereto at the dosages and concentrations employed. Often, the pharmaceutically acceptable carrier is an aqueous pH buffered solution, which is useful for drug delivery, particularly for the delivery of antibody molecules. The pharmaceutical composition may be formulated by mixing the active agent with carriers and optionally other agents that are usually incorporated into the formulation. For example, the composition may be formulated in the form of lyophilized formulations, aqueous solutions, dispersions or solid preparations.

The present invention also encompasses the administration of the pharmaceutical composition to a subject in need thereof, particularly a human patient suffering from a neurodegenerative disorder, such as Parkinson's disease or DLB. Depending on the type and the severity of the condition to be treated about 1 μg/kg to 15 mg/kg of the active ingredient may be administered to a patient in need thereof, e.g. by one or more separate administrations or by continuous infusion. A typical daily dosage might range from about 1 μg/kg to about 100 mg/kg, depending on the factors mentioned above. For repeated administrations over several days or longer, depending on the condition to be treated, the treatment is sustained until a desired suppression of the disease or the symptoms occurs. The composition may be administered by any suitable route, for example, by parenteral, subcutaneous, intranasal, intravascular, intravenous, intraarterial, or intrathecal injection or infusion.

The active agent according to the present invention may be administered together with other active agents, particularly active agents useful for the treatment of neurodegenerative disorders, such as PD or DLB.

Furthermore, the present invention relates to a diagnostic method comprising determining the amount and/or localization of α-Syn in the patient tissue or a patient sample. In this embodiment, the antibody of the present invention preferably carries a labelling group as described above.

Finally, the present invention relates to kits for diagnosis or treatment of neurodegenerative disorders comprising at least one antibody and/or nucleic acid molecule and/or cell as described above. In addition, the kit further comprises at least one other active agent or further components.

The present invention shall be explained in more detail by the following figures and examples.

FIGURE LEGENDS

FIG. 1: Naturally occurring α-Syn-Abs were isolated from the serum of a single donor (30.6 mg/ml starting material) and from a commercially available IVIG preparation (Octagam; 10 mg/ml starting material) using affinity chromatography. The fractions that resulted from a representative experiment are depicted.

FIG. 2: The fractions that resulted from the chromatography column were analyzed in an α-Syn ELISA. The main fractions (MF) with high IgG content were compared to the peripheral fractions (PF) that contained less IgG. As a negative control, the flow through (FT) from the affinity purification was analyzed. Samples were added to α-Syn-coated wells of an ELISA plate. Bound antibodies were detected with a HRP-conjugated goat anti-human IgG antibody followed by Tetramethylbenzimide (TMB)/peroxidase colour reaction that was detected at 450 nm (Pierce Biotechnologies). A. Fractions containing α-Syn-Abs compared to fractions without α-Syn-Abs and to flow through of the affinity chromatography. B. α-Syn-Abs isolated from IVIG versus α-Syn-Abs isolated from the serum of a single donor.

Figure 3:
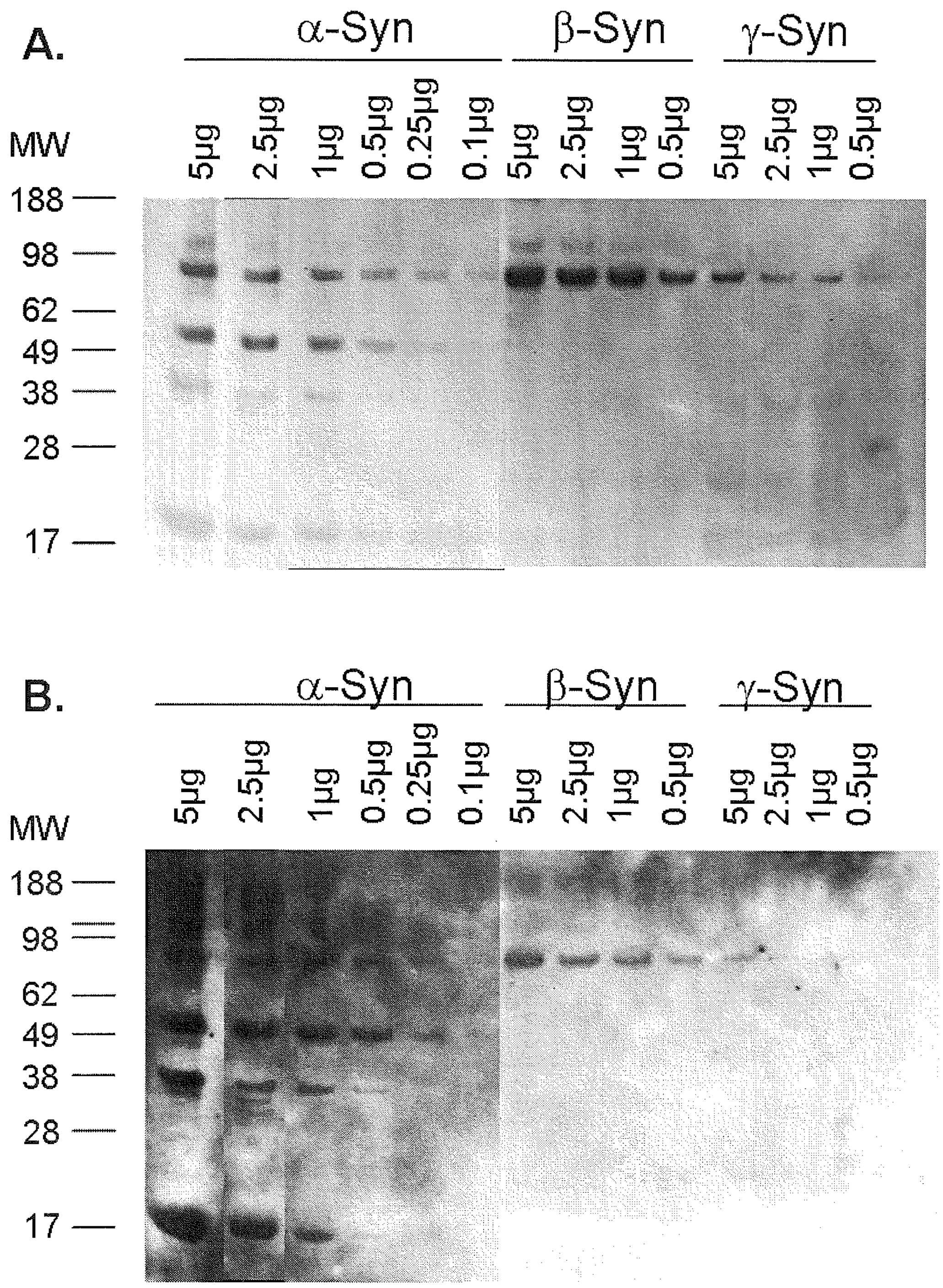

FIG. 3: SDS-Page and Western blot analysis of naturally occurring α-Syn-Abs.

Different amounts of recombinant α-Syn (5 μg, 2.5 μg, 1 μg, 0.5 μg, 0.25 μg, and 0.1 μg), β-Syn (5 μg, 2.5 μg, 1 μg, and 0.5 μg) and γ-Syn (5 μg, 2.5 μg, 1 μg, and 0.5 μg) were separated on a 4-12% gradient mini gel (Invitrogen) and detected by: A. Naturally occurring α-Syn-Abs isolated from IVIG, and B. Naturally occurring α-Syn-Abs isolated from the serum of a single donor.

Figure 4:
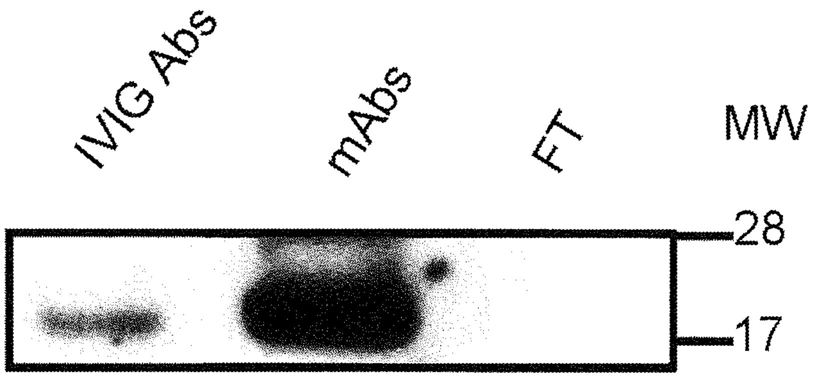

FIG. 4: Immunoprecipitation of α-Syn by α-Syn-Abs affinity-purified using IVIG. Naturally occurring α-Syn-Abs isolated from IVIG, positive control with a commercially available monoclonal α-Synuclein antibody (clone Syn 211, Biosource) and a negative control (flow through from the affinity purification) were immunoprecipitated with α-Syn and subjected to Western blot analysis. Data shown are from a representative experiment.

FIG. 5: Surface plasmon resonance analysis of affinity-purified polyclonal α-Syn-Abs (analyte) to α-Syn was done on BIACORE 2000 (Biacore AB) at 25° C. A. Interaction analysis of immobilized α-, β- and γ-Syn with affinity-purified α-Syn-Abs (pAB). Plot of sensograms of antibody binding to α- (red; top graph), to β- (blue; middle graph) and γ-Syn (green; bottom graph). B. Interaction analysis of immobilized α-, β- and γ-Syn with a monoclonal antibody against human α-Syn (mAB; Syn 211 Biosource). Plot of sensograms of antibody binding to α- (red; top graph), to β- (blue; middle graph) and γ-Syn (green; bottom graph).

Figure 6:
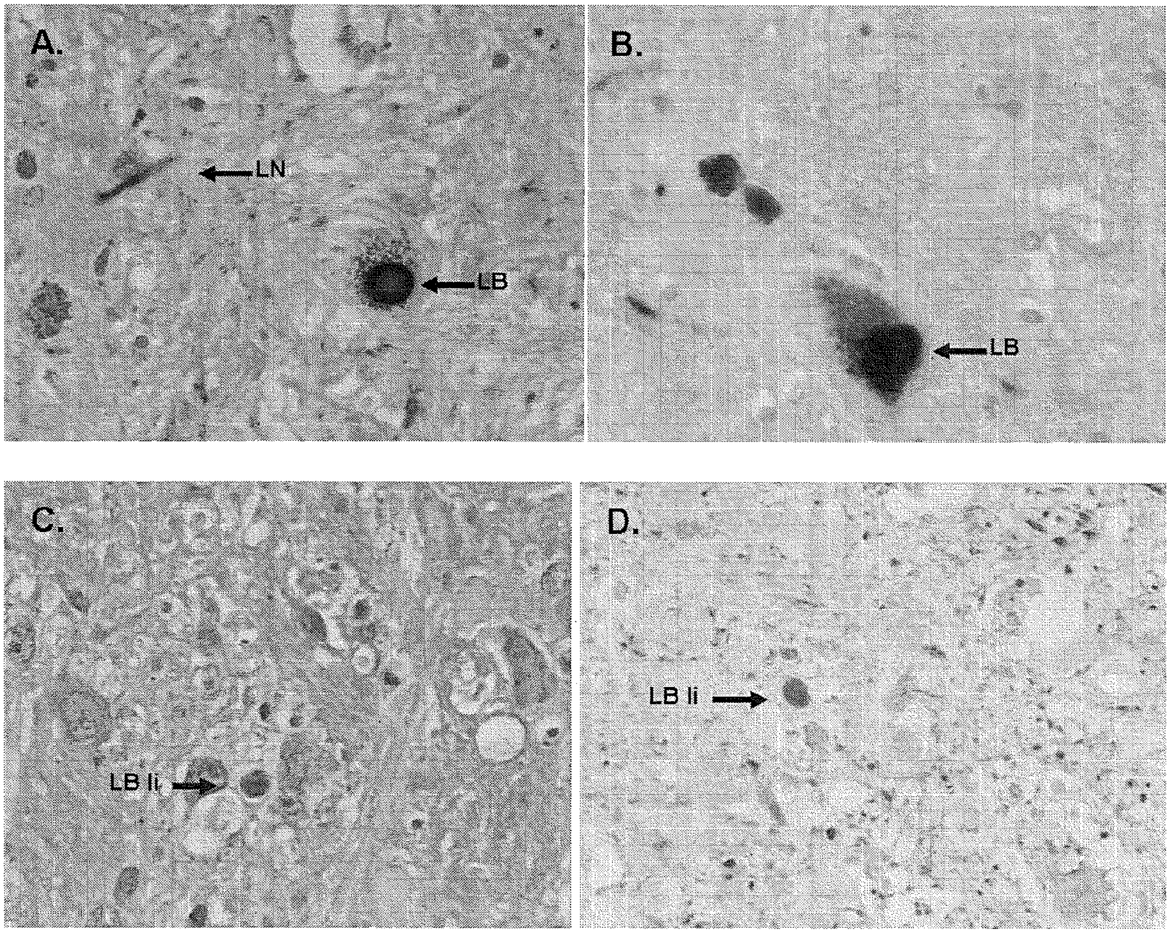

FIG. 6: Immunohistochemical detection of α-Syn in a brain sample of a patient with Parkinson's disease (PD). A. Immunostain of a brain sample of a human PD case (left panel) using the naturally occurring α-Syn-Ab. B. Immunostain (positive control) of a brain sample of a human PD case (right panel) incubated with a commercially available α-Syn monoclonal antibody (mAb) (MBL clone 211). C. Immunostain of a brain sample of a transgenic mouse model using the affinity-purified α-Syn-Ab. D. Immunostain (positive control) of a brain sample of a transgenic mouse model incubated with a commercially available α-Syn-mAb (MBL clone 211). LB stands for Lewy body, LN for Lewy neurites and LB li for Lewy body like inclusions.

Figure 7:
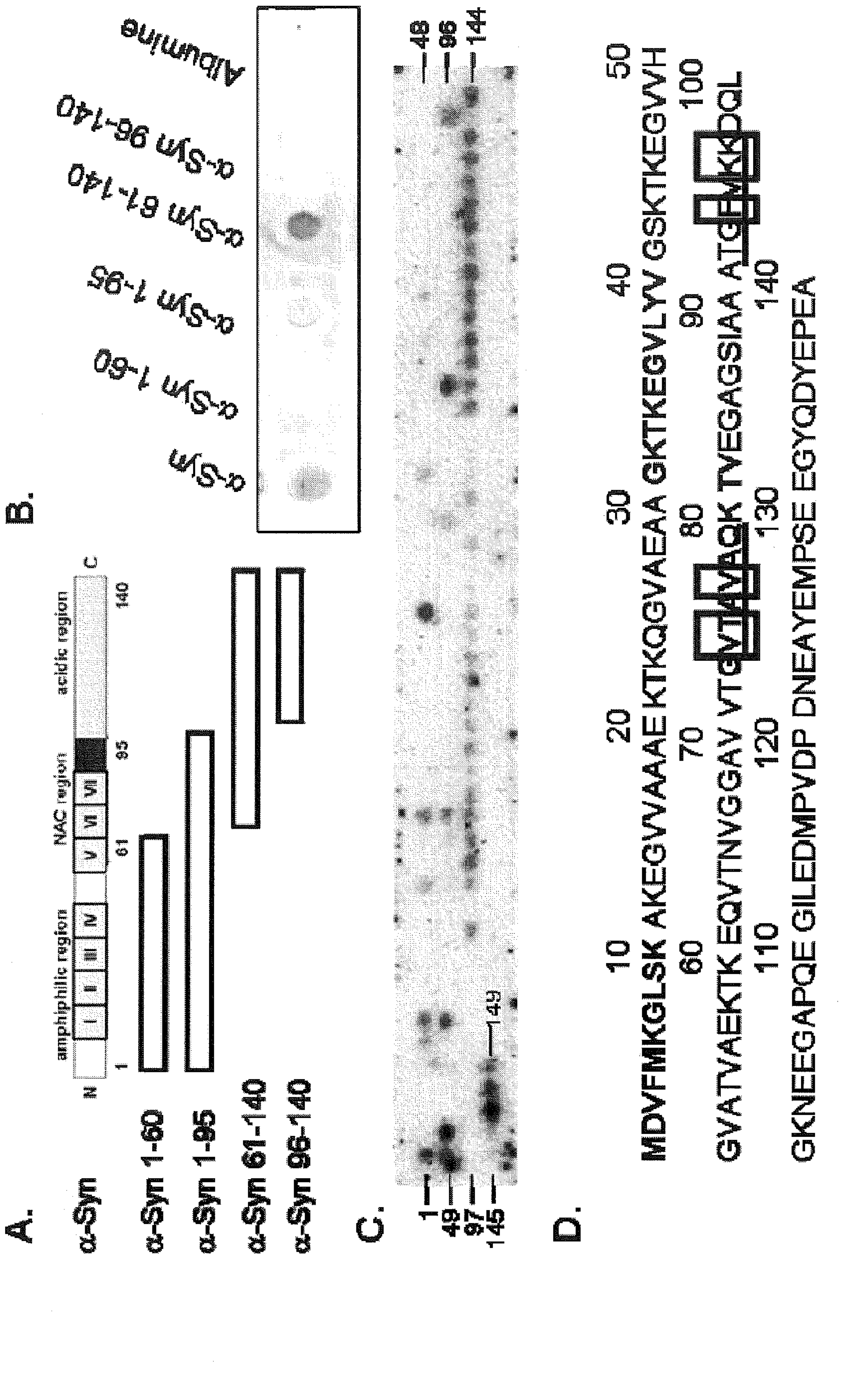

FIG. 7: A. α-Syn sequence. Epitope Mapping of α-Syn-nAbs using Dot Blot analysis (B.) and a Peptide Array (C.). Results are summarized in D., which shows SEQ ID NO.: 1, with the relevant sequences highlighted in bold characters and relevant amino acids as determined by an alanine scan in boxes.

FIG. 8: α-Syn specific IgG1 heavy chain variable domain amino acid sequences. All amino acid sequences displayed as consensus sequence for the anti-α-Synuclein $HC_v$ molecules including the associated CDR regions were found in the shown arrangement in vivo. The consensus sequence reflects the ones found most often from the alpha synuclein specific B-cells analyzed. Positions with amino acid variants indicating additional specific antibody subtypes are highlighted. Possible amino acid exchanges are shown below the Anti-α-Synuclein $HC_v$ sequence. Here, anti-α-Synuclein HCv Type 1 sequences are shown. 48 sequences derived from 80 clones were analyzed. These 48 clones attributed to $HC_v$ Type 1 correspond to 60% of all analyzed IgG sequences. 4% of all Type 1 sequences are identical to the consensus sequence, 27% show a maximum exchange of 2 amino acids. Linked amino acid exchanges are shown within one box. CDR1(SEQ ID NO.: 3)/CDR2 (SEQ ID NO.: 4)/CDR3 (SEQ ID NO.: 5 and 6) of anti-α-Synuclein $HC_v$ Type 1 antibodies in the combinations detected in blood derived B-cells are shown in Table 1.

FIG. 9: α-Syn specific IgG1 heavy chain variable domain amino acid sequences. Further details are specified in the legend to FIG. 8. Here, anti-α-Synuclein HCv Type 2 sequences are shown. 13 sequences derived from 80 clones were analyzed. These 13 clones attributed to $HC_v$ Type 2 correspond to 15% of all analyzed IgG sequences. 67% of all Type 2 sequences are identical to the consensus sequence; 17% show a maximum exchange of 1 amino acid. Linked amino acid exchanges are shown within one box. CDR1(SEQ ID NO.: 7)/CDR2 (SEQ ID NO.: 8)/CDR3 (SEQ ID NO.: 9 and 10) of anti-α-Synuclein $HC_v$ Type 2 antibodies in the combinations detected in blood derived B-cells are shown in Table 2.

FIG. 10: α-Syn specific IgG1 heavy chain variable domain amino acid sequences. Further details are specified in the legend to FIG. 8. Here, anti-α-Synuclein HCv Type 3 sequences are shown. 19 sequences derived from 80 clones were analyzed. These 19 clones attributed to $HC_v$ Type 3 correspond to 24% of all analyzed IgG sequences. 37% of all Type 3 sequences are identical to the consensus sequence, 10% show a maximum exchange of 2 amino acids. Linked amino acid exchanges are shown within one box. CDR1(SEQ ID NO.: 11)/CDR2 (SEQ ID NO.: 12)/CDR3 (SEQ ID NO.: 13 and 14) of anti-α-Synuclein $HC_v$ Type 3 antibodies in the combinations detected in blood derived B-cells are shown in Table 3.

FIG. 11: Naturally occurring α-Syn specific kappa light chain variable domain amino acid sequences. All amino acid sequences displayed as consensus sequence for the anti-α-Synuclein $LC_v$ molecules including the associated CDR regions were found in the shown arrangement in vivo. The consensus sequence reflects the ones found most often from the alpha synuclein specific B-cells analyzed. Positions with amino acid variants indicating additional specific antibody subtypes are highlighted. Possible amino acid exchanges are shown below the anti-α-Synuclein $LC_v$ sequence. Here, anti-α-Synuclein $LC_v$ Type 1 sequences are shown. 64 sequences derived from 125 clones were analyzed. These 64 clones attributed to $LC_v$ Type 1 correspond to 51% of all analyzed IgG sequences. 48% of all Type 1 sequences are identical to the consensus sequence, 50% show a maximum exchange of 1 amino acid. Linked amino acid exchanges are shown within one box. CDR1(SEQ ID NO.: 15)/CDR2 (SEQ ID NO.: 16)/CDR3 (SEQ ID NO.: 17 and 18) of anti-α-Synuclein $LC_v$ Type 1 antibodies in the combinations detected in blood derived B-cells are shown in Table 4.

FIG. 12: Naturally occurring α-Syn specific kappa light chain variable domain amino acid sequences. Further details are specified in the legend to FIG. 11. Here, anti-α-Synuclein $LC_v$ Type 2 sequences are shown. 24 sequences derived from 25 clones were analyzed. These 24 clones attributed to $LC_v$ Type 2 correspond to 19% of all analyzed IgG sequences. 38% of all Type 2 sequences are identical to the consensus sequence. Linked amino acid exchanges are shown within one box. CDR1(SEQ ID NO.: 19)/CDR2 (SEQ ID NO.: 20)/CDR3 (SEQ ID NO.: 21 and 22) of anti-α-Synuclein $LC_v$ Type 2 antibodies in the combinations detected in blood derived B-cells are shown in Table 5.

FIG. 13: Naturally occurring α-Syn specific kappa light chain variable domain amino acid sequences. Further details are specified in the legend to FIG. 11. Here, anti-α-Synuclein $LC_v$ Type 3 sequences are shown. 33 sequences derived from 125 clones were analyzed. These 33 clones attributed to $LC_v$ Type 3 correspond to 26% of all analyzed IgG sequences. 36% of all Type 3 sequences are identical to the consensus sequence, 9% show a maximum exchange of 2 amino acids. Linked amino acid exchanges are shown within one box. CDR1(SEQ ID NO.: 23)/CDR2 (SEQ ID NO.: 24)/CDR3 (SEQ ID NO.: 25 and 26) of anti-α-Synuclein $LC_v$ Type 3 antibodies in the combinations detected in blood derived B-cells are shown in Table 6.

Figure 14:
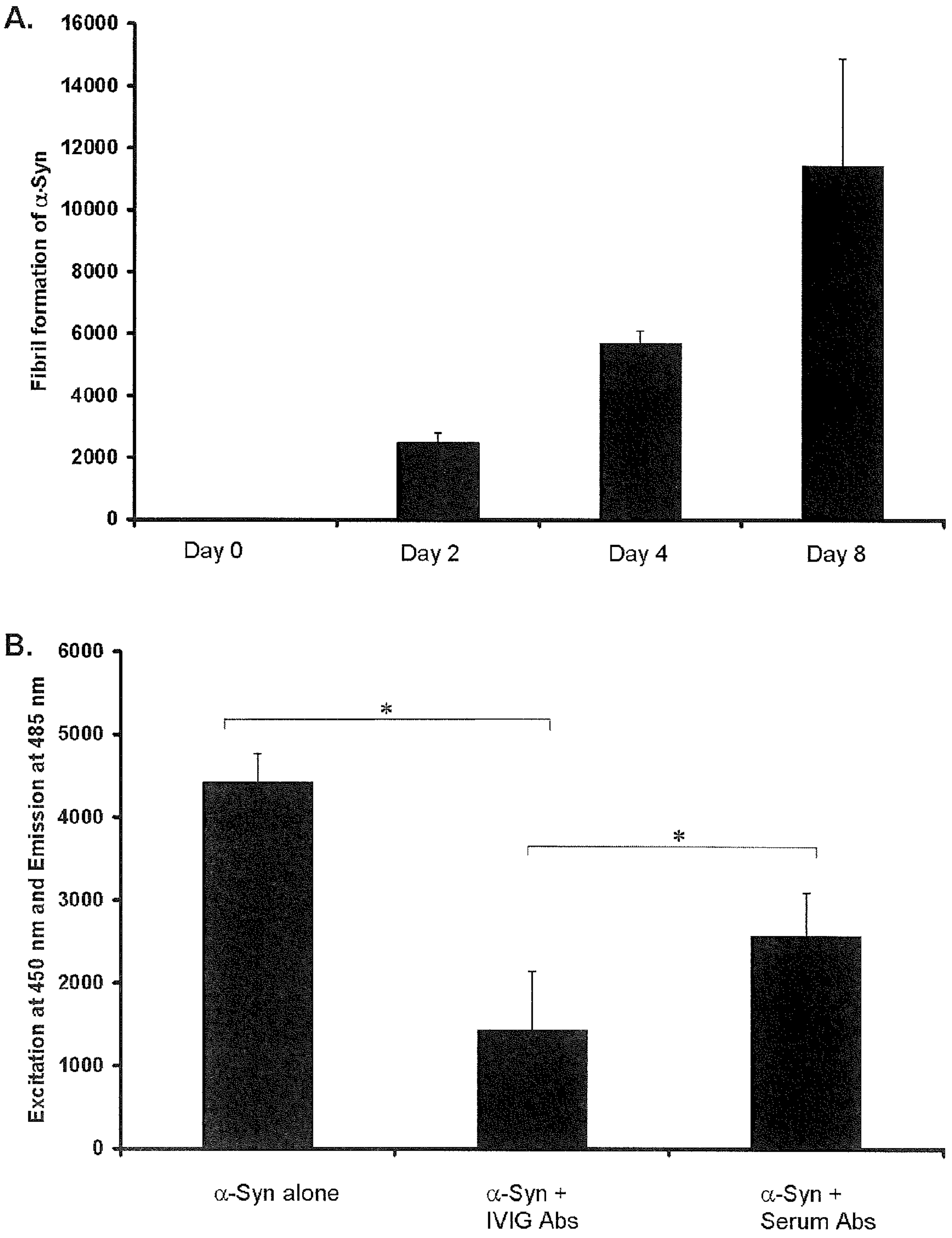

FIG. 14: Effect of α-Syn-Abs on aggregation of α-Syn. The kinetics of α-Syn fibril formation was monitored by Thioflavin T (ThT) fluorescence. α-Syn (rPeptide; 4 mg/ml) was shaken at 37° C. and 600 rpm. A. At the time points indicated, aliquots were taken and a ThT assay was performed. B. α-Syn was incubated with or without the α-Syn-Abs affinity-purified from IVIG or from the serum of a single donor (1 μM; Serum Abs). The samples were incubated four days at 37° C. and 600 rpm and aliquots were added to the ThT solution. ThT fluorescence intensity was measured at an excitation wavelength of 450 nm and an emission wavelength of 485 nm. Samples were run in triplicates and plotted as means+/−SD. A comparison of the cells treated with α-Syn alone to cells treated with either α-Syn Abs from IVIG or α-Syn Abs from serum was performed using a t-test (* $p<0.05$).

Figure 15:
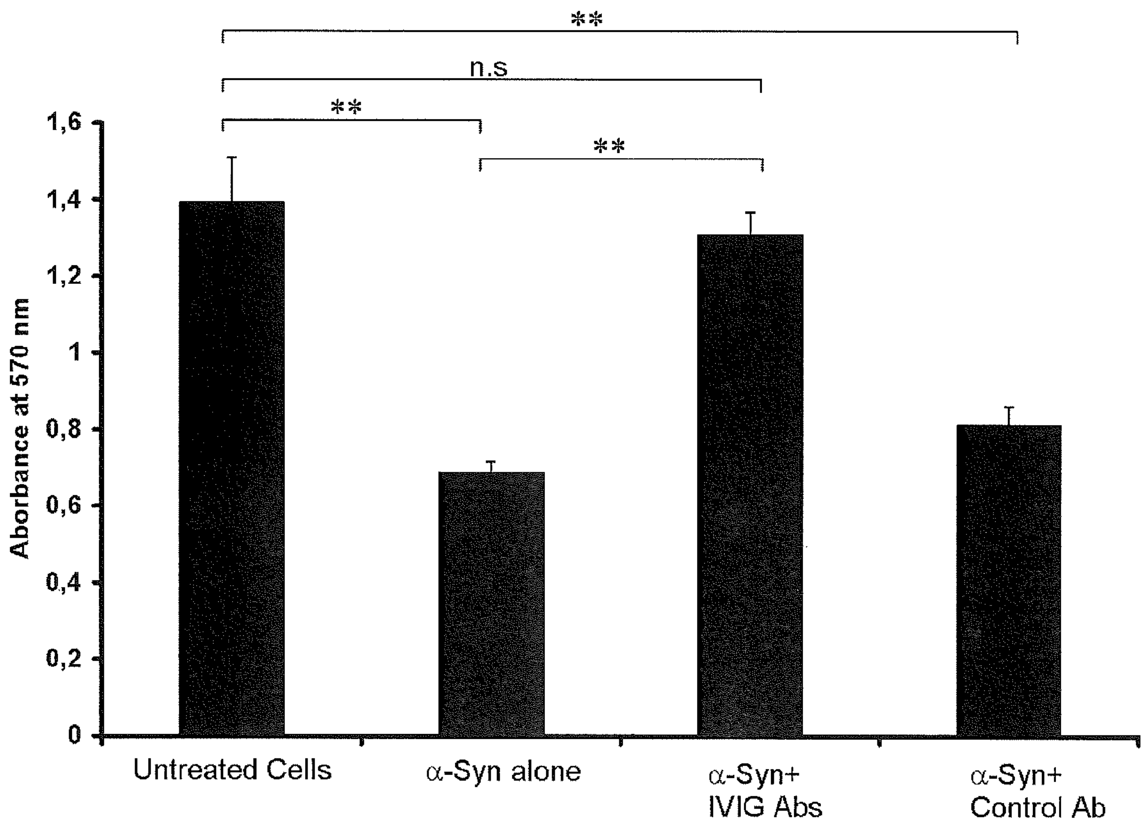

FIG. 15: Effect of the affinity-purified α-Syn-Abs on α-Syn-induced cytotoxicity. SH-SY5Y cells were treated with 10 μM aliquots of α-Syn aggregated with and without 1 μM affinity-purified IVIG α-Syn-Abs or a synthetic antibody against a growth factor receptor protein as a non-specific control. Samples were run in triplicates and plotted as means+/− SD. A comparison between every group in the assay was performed using the ANOVA Tukey test (** $p<0.001$), n.s. is not specific.

EXAMPLES

1. Materials and Methods

1.1 Isolation and Purification of Naturally Occurring α-Synuclein Antibodies Naturally occurring α-Synuclein antibodies (α-Syn-Abs) were isolated using affinity chromatography. A column was packed with $NH_2$-activated resin (PIERCE Biotechnology, Rockford, Ill.), labelled with recombinant α-Syn (rPeptide, Bogart, Ga.; 1 mg/2 ml drained resin) and equilibrated and washed with phosphate buffered saline (pH 7.4). After passing either purified human intravenous immunoglobulin G (IVIG) or IgG fraction from the plasma of a healthy donor through the column, sixteen fractions were eluted with glycine buffer at pH 2.8 and collected. The main fractions that contain the greatest amount of α-Syn-Abs as well as the peripherical fractions that contain low amounts of α-Syn-Abs were pooled and their binding capacity was tested using an α-Syn-ELISA.

1.2 α-Syn-ELISA

A 96-well ELISA plate was coated with recombinant α-Syn (rPeptide) dissolved in coating buffer (1.7 mM $H_2PO_4 \times H_2O$; 98 mM $Na_2HPO_4 \times H_2O$; 0.05% sodium azide, pH 7.4). After blocking the plate with SuperBlock blocking buffer (PIERCE Biotechnology), α-Syn-Abs samples were loaded overnight at 4° C. An appropriate secondary antibody, goat anti-human IgG H+L peroxidase conjugate (Calbiochem; Merck KGaA, Darmstadt, Germany), was incubated for one hour. Tetramethylbenzimide (TMB, Calbiochem) was added, and the reaction was stopped with 2N $H_2SO_4$. Finally, measurement was carried out in an ELISA plate reader (Multiskan Ex, Thermo, Waltham, Mass.) at 450 nm.

1.3 Protein Gel Analysis

Samples were mixed with 4×LDS sample buffer (Invitrogen, Karlsruhe, Germany) with DTT, boiled for 5 min and subjected to polyacrylamide gel electrophoresis. Samples were separated on NUPAGE Bis-Tris 4-12%, 1 mm gels (Invitrogen) in MES running buffer at 160 V according to the manufacturer's instructions. Once separated, the proteins were either visualized using silver staining or subjected to a Western blot analysis.

1.4 Western Blot Analysis

After being separated, the proteins were transferred to a PVDF membrane at 160 mA for 45 min. Membranes were blocked using RotiBlock (Roth, Karlsruhe, Germany) for 2 h at room temperature and were then probed overnight with either affinity-purified α-Syn-Abs 1:20,000 in RotiBlock or monoclonal α-Syn-Abs (clone Syn211, Invitrogen) 1:20,000 in RotiBlock, as indicated. The membranes were then washed three times in 1× phosphate buffered saline with 0.05% Tween 20 (PBST) and incubated with the appropriate secondary antibody, goat anti-human or goat anti-mouse (Pierce Biotechnology), at a concentration of 1:100,000 in PBST for 1 h at room temperature. Proteins were visualized using SuperSignal West Dura (PIERCE Biotechnology).

1.5 Immunoprecipitation of α-Synuclein by Affinity-Purified α-Syn-Abs

The reaction mixture of α-Synuclein was incubated with affinity-purified α-Syn-Abs, monoclonal α-Syn-Abs (as positive control, clone Syn 211, Invitrogen), phosphate buffered saline (PBS), and flow through from the affinity chromatography (as negative control) at 4° C. overnight. Protein G was added and incubated at 4° C. overnight to precipitate the IgG/α-Syn complex. The precipitates were centrifuged and washed five times with PBS before loading a 12% SDS gel. In the Western blot, α-Syn monoclonal antibody clone 211 (Invitrogen) and HRP-conjugated goat anti-human IgG were used and this was then followed by detection with West Dura Super Signal (PIERCE Biotechnology).

1.6 Surface Plasmon Resonance

Surface Plasmon Resonance (SPR) analysis of the affinity-purified polyclonal α-Syn-Abs binding to α-Synuclein was done on BIACORE 2000 (GE Healthcare, Freiburg, Germany). Ligand immobilization of α-, β- and γ-Synuclein (Sigma Aldrich, Munich, Germany) resuspended in 1×PBS; 10-20 μg/ml) was performed by amino coupling to 10,000 units (RU) on different flow cells (Fc2-4) of the CM5 sensor chip. β- and γ-Synuclein were used as negative controls. The SPR-signal of the reference flow cell (Fc1) was automatically subtracted from the sensograms of any other flow cell. Interaction analysis was performed by injection of analyte samples (IVIG, 75-150 μg/ml) or α-Syn monoclonal antibody clone Syn 211 (Invitrogen, 10 μg/ml as positive control; 20 μl/min) diluted in running buffer (1×PBS/0.005% P20). The sensor chip was cleaned from immune-complexes by the injection of 5-20 μl of regeneration solution (25 mM NaOH). Sensogram evaluation was performed using the BIA evaluation 3.2 RCl.

1.7 Epitope Mapping

In order to map detailed epitopes of the affinity-purified α-Syn-Abs, we used four peptides that spanned the whole sequence of α-Syn. The α-Syn-Abs were tested for binding capability to peptides Syn 1-60, Syn 61-140, Syn 1-95, Syn 96-140 (Sigma Aldrich) using Western blot and surface plasmon resonance as described above, with α-Syn-Abs as the ligand and the Synuclein truncations as analytes.

In an additional set of experiments, we represented α-synuclein as an array of overlapping peptides using the SPOT technology of multiple peptide synthesis. Specifically, a series of decamer peptides was assembled in an array format on a nitrocellulose membrane by walking through the entire α-synuclein sequence with a sliding window of six amino acids (FIG. 7). A total of 23 peptide spots were generated to cover the entire α-synuclein sequence. These spots were numbered sequentially from 1-23. In addition to the overlapping peptides we added a version with an amino acid randomly changed, numbered 25-47 as well as a scrambled version, numbered 49-71 of the same peptides. We performed an alanin scan of the NAC region of α-synuclein. The corresponding peptides were added to the membrane.

Subsequently, the α-synuclein peptide array was probed with α-Syn-nAbs and spots on the array produced binding signals.

1.8 Immunohistochemistry

In order to determine the cellular and subcellular localization of the binding partners of the α-Syn-Abs in the brain of transgenic mice (Thy1)-h[A30P] (Kahle et al., 2004), immunohistochemical experiments were conducted using brain samples of patients with Parkinson's disease and a neuroblastoma cell line (SH-SY5Y). The histopathological staining properties of α-Syn-Abs were compared to those of commercially available paraffin permeable antibodies against α-Synuclein (clone 211, MBL, Woburn, Mass., USA). Briefly, antigen retrieval was carried out by incubation in 70% formic acid for 20 min. After quenching of the endogenous peroxidase by 3% $H_2O_2$ in Methanol for 20 min the primary antibodies were incubated in a 1:100 dilution at 37° C. in a humid chamber for 1 hr. As a detection system, the Vectastain Elite ABC kit or the Vectastain M.O.M. kit (Biozol, Eching, Germany) was used according to the manufacturer's instructions.

1.9 α-Synuclein Fibril Formation

The generation of fibrillated α-Syn was performed as described previously (Herrera et al., 2008). Briefly, recombinant α-Syn (rPeptide) was diluted in 10 mM Tris buffer of pH 7.4 and shaken at 37° C. and 600 rpm. At different time points (0, 2, 4 and 8 days), aliquots were taken and measured using the Thioflavin T fibrillation assay. In order to determine the ideal α-Syn concentration for the assay, several concentrations (4, 2, 1 mg/ml) were tested after four days of incubation.

1.10 Thioflavin T Fibrillation Assay

In order to determine the amount of fibrillated α-Syn, a fluorometric experiment was performed as described previously (Herrera et al., 2008). Recombinant α-Syn (rPeptide) was incubated as described above. In this case, 10 μl aliquots were added to 80 μl 50 mM glycine puffer of pH 8.5 and 10 μl 100 μM Thioflavin T solution (Sigma Aldrich) and fluorescence was measured spectrofluorometrically using a Tecan reader Infinite M200 (Crailsheim, Germany) at an excitation wavelength of 450 nm and an emission wavelength of 485 nm. Samples were run in triplicates and plotted as means+/− SD. Each experiment was performed at least three times.

1.11 Cell Culture and Toxicity Assay

Human neuroblastoma cells (SH-SY5Y) were maintained in RPMI1640 (Lonza, Cologne, Germany) supplemented with 10% (v/v) fetal calf serum and 1% (v/v) penicillin/streptomycin antibiotic mix and grown in a 5% $CO_2$ atmosphere at 37° C. Cells were harvested and plated in 96-well plates coated with poly-L-Lysin at 20,000 cells per well per 100 μl of medium. Cells were then treated with α-Syn alone or α-Syn pre-incubated with α-Syn-Abs for four days at 37° C. and 600 rpm. The MTT (3-(4,5-dimethylthiazol-2-yl)-2,5-diphenyltetrazolium bromide; Sigma Aldrich) reagent was resuspended in 5 mg/ml with deionised water and diluted in cell culture media to 0.5 mg/ml. Treatment was removed from the cells and 200 μl MTT solution was added and incubated for 2-4 hours at 37° C. After removal of the MTT solution, cells were treated with 200 μl DMSO to reduce the tetrazolium salt into the insoluble, purple coloured formazane. Readings were taken at 570 nm after another 30 min incubation at room temperature and again in the dark using a Tecan reader. Samples were run in triplicates and plotted as means+/− SD. Each experiment was performed at least three times.

1.12 De Novo Amino Acid Sequencing of One Purified Human Antibody Against Human α-Synuclein 1.12.1 Reduction and Alkylation of Disulfide Bonds Protein samples were resolubilized in 50 mM triethylammonium bicarbonate (TEAB) buffer prior to reduction by addition of tris(2-carboxyethyl)phosphine (TCEP) to a final concentration of 5 mM and incubation at 37° C. for 20 min. Subsequently iodoacetamide to a 10 mM final concentration was added and the sample was incubated at room temperature for another 20 mins in the dark.

1.12.2 SDS-PAGE

Separation of antibody light chain molecules and heavy chains molecules was performed by SDS-PAGE according to Laemmli et al. For subsequent proteolytic cleavage of the light chain IgG molecules small gel spots were cut and washed according to Proteome Factory's (Berlin, Germany) in-gel digestion protocol.

1.12.3 Enzymatic Cleavage

Alkylated peptides were used for enzymatic cleavage with trypsin, chymotrypsin, glutamic-C protease, clostripain, LysC or proteinase K. Therefore a small aliquot was diluted with 10 volumes of the suitable buffer for the enzymatic cleavage. Incubation time was varied in order to produce overlapping peptides by each protease.

Buffer solutions: Trypsin, Thermolysin, LysC: 50 mM ammonium bicarbonate, 10% acetonitrile (v/v) Chymotrypsin: 100 mM Tris-HCl, 10 mM $CaCl_2$, 5% ACN (v/v), pH 8.0

Proteinase K: 100 mM Tris-HCl, 10 mM $CaCl_2$, 5% ACN (v/v), pH 8.0 Glutamic-C protease: 50 mM Tris-HCl, 0.5 mM Glu-Glu, pH 8.0 Clostripain: 50 mM Tris-HCl, 10 mM $CaCl_2$, 10% ACN (v/v), 20 mM DTT, pH 8.5

1.12.4 Mass spectrometry (MS)

For carrying out nanoLC-ESI-MS/MS high resolution MS, the HPLC system was coupled to an Advion NanoMate 100 chip-electrospray system (Advion, Ithaca, N.Y.), and detection was performed on a Finnigan LTQ-FT mass spectrometer (ThermoFisher, Bremen, Germany) equipped with a 6 T magnet. Peptides from enzymatic cleavage were acidified with formic acid and applied to nanoLC-ESIMS/MS. After trapping and desalting the peptides on enrichment column (Zorbax SB C18, 0.3×5 mm, Agilent) using 1% acetonitrile/0.5% formic acid solution for five minutes peptides were separated on Zorbax 300 SB C18, 75 μm×150 mm column (Agilent, Waldbronn) using an acetonitrile/0.1% formic acid gradient from 5% to 40% acetonitrile within 40 to 115 minutes. MS overview spectra were automatically taken in FT-mode (+/− 3 ppm) according to manufacturer's instrument settings for nanoLC-ESI-MSMS analyses, peptide fragmentation and detection was accomplished in the instrument's LTQ ion trap with an accuracy of +/− 0.3 Da.

1.12.5 Database Search

The peptide masses and fragmentation data was searched against a human antibody sequenced derived from the NCBInr (National Center for Biotechnology Information, Bethesda, USA) database utilizing the MASCOT search engine (Matrix Science, London). Positive identification of peptides were annotated for the generation of sequence candidates.

Unassigned data was extracted and used for subsequent de novo peptide sequencing and searching of amino acid permutated human antibody peptide amino acid sequences.

1.12.6 Search Parameters

MS parent ion accuracy +/− 3 ppm

MSMS fragment ion accuracy +/− 0.3 Da

Fixed modification: Carbamidomethylation (Cys)

Denovo sequencing

Binning of duplicate spectra and peaks:

Binning MS 0.00015%

Binning MSMS 0.15 Da

Sequencing parameters:

Tolerance MS 0.0003%

Tolerance MSMS 0.3 Da

Candidate sequences were subjected to the Basic Local Alignment Search Tool (BLAST)

BLAST search parameters:

BLAST matrix: PAM30

Expect value: 10

Database: Human antibody sequences derived from NCBInr

HPLC separation of peptides

HPLC separation of LysC digested peptides was performed by using an Agilent 1100 HPLC system with a Zorbax 300SB-C8 column (150×2.1 mm) and a micro fraction collector for automatic peak fractionation. Solvent A was 0.1% TFA in water and solvent B 0.1% TFA in acetonitrile. The gradient started at 0% B for 5 minutes followed by increasing concentrations of B to 10 at 10 min, 40% at 55 min, 60% at 65 min and 100% at 70 minutes.

1.12.7 N-terminal Edman Sequencing

N-terminal Edman sequencing of HPLC separated peptides was performed by an ABI Procise Model 49× protein sequencer using peptide fractions spotted on to Biobrene treated glass fiber discs.

2. Results 2.1 Isolation of Naturally Occurring α-Syn-Abs From IVIG and Serum of a Single Donor We purified human α-Syn-Abs from IVIG and from the serum of a single donor by using an affinity column coated with recombinant α-Syn (FIG. 1). The resulting fractions with the highest IgG content were pooled and their binding properties to α-Syn were tested using an ELISA. We found that the resulting main fractions had a strong anti-α-Syn signal as compared to both the flow through IgG and peripheral fractions without α-Syn-Abs (FIG. 2*a*). There was a 2.5-fold increase in the fraction containing affinity-purified α-Syn-Abs as compared to the peripheral fractions without the antibody and a 4-fold increase as compared to the flow through of the affinity column. In FIG. 2*b* we show that α-Syn-Abs isolated from IVIG as well as from the serum of a single donor are dose-dependently binding α-Syn in an ELISA. The detection limit lies between 125 and 62.5 ng/ml for both affinity purified α-Syn-Abs.

2.2 Binding Specificity of the Affinity-Purified α-Syn-Abs From IVIG and Serum

The purified α-Syn-Abs from IVIG and that from single donor serum were able to detect the monomeric form of recombinant α-Syn peptide at 19 kDa on Western blots in a dose dependent manner. It also detected aggregated α-Syn species (FIGS. 3*a* and 3*b*). The signals at 38, 57 and 76 kDa correspond to the approximate sizes of dimeric, trimeric and tetrameric forms of α-Syn, respectively. A tetrameric form of β- and γ-Syn corresponding to the 76 kDa band was clearly recognized by α-Syn-Abs from IVIG and from serum.

In order to further confirm the ability of the naturally occurring α-Syn-Abs to bind α-Syn, we performed immunoprecipitation of recombinant α-Syn peptide (FIG. 4). We were able to confirm that the affinity-purified α-Syn-Abs do bind α-Syn peptide. The negative control, consisting of the same immunoprecipitation reaction with the column flow-through alone, did not bind to the recombinant α-Syn peptide. The reactions with protein G alone or with non-specific antibodies (Interleukin-1 antibody) were also negative (data not shown).

Furthermore, we obtained SPR data on the interaction of affinity-purified α-Syn-Abs from IVIG with α-, β- and γ-Synuclein immobilized via amino coupling (FIG. 5). Data demonstrated that the affinity-purified α-Syn-Abs from IVIG bind to α-Syn, to some extent as well as to β-Syn, but not to γ-Syn. After 20 seconds, the antibody dissociates to 50% from α-Syn and 100% from the β-isoform. In comparison, a monoclonal antibody (clone Syn 211, Biosource) against human α-Syn bound particularly strong to α-Syn but bound very little or not at all to β-Syn and γ-Syn.

2.3 Affinity-Purified Antibodies Recognize α-Synuclein in Lewy Bodies—Immunohistochemical Experiments In order to display the anatomical and histopathological localization of α-Syn in Lewy bodies using affinity-purified α-Syn-Abs, brain samples from PD patients and from an α-Syn transgenic (Thy1)-h[A30P] mouse model were analyzed using immunohistochemistry. In human PD patient samples, the affinity-purified α-Syn-Abs recognized the same structures as the monoclonal anti-human α-Syn-Ab (FIG. 6); these included a halo around a weaker core in Lewy bodies and drilled roots in Lewy neurites as well as in somatodendritic deposits. In the α-Syn transgenic mouse model there are no Lewy bodies present but rather only so called "Lewy body like inclusions" have been reported (Kahle et al., 2001). The immunohistochemical staining demonstrated that both the affinity purified α-Syn-Abs and the monoclonal α-Syn-Ab recognised these inclusions. Taken together, our results could conclusively demonstrate the specific binding of the affinity-purified antibodies to either recombinant human α-Syn or native human α-Syn.

2.4 Epitope Mapping

In order to further characterize the naturally occurring antibodies, we identified which epitopes of α-Syn are bound by α-Syn-Abs. Therefore, four truncated synthetic peptides spanning different regions of α-Syn were subjected to Western blot analysis (FIG. 7*a*). The α-Syn-Abs bound to the peptides corresponding to residues 1-60, 1-95 and 61-140 but not to the peptide corresponding to residues 96-140 (FIG. 7*b*).

Dot Blot analysis (FIG. 7) shows that the α-Syn-nAbs bind to the full-length α-synuclein but not to the albumin control. The strongest signal is observed with the peptide corresponding to residues 61-140. There is a very slight binding to the peptide corresponding to residues 1-60 and 1-95, and no binding to the peptide corresponding to residues 96-140 (FIG. 7).

Inspection of the decamer peptide array revealed positive signals for peptides 1, 7, 13 and 16. corresponding to the sequences listed in Table 7.

TABLE 7

List of α-synuclein peptides that showed significant binding to α-Syn-nAbs in the peptide array membrane. The missing aa sequences 2, 25, 26, 34, 36, and 61 were not positive and are therefore marked with -.

| Sequence | One aa change | scrambled |
|---|---|---|
| 1 MDVFMKGLSK | 25 — | 49 MMVGKSDLKF |
| 2 — | 26 — | 50 LESVGAKVKG |
| 7 VLYVGSKTKE | 31 VLYVGSKT>MKE | 55 VYSVLKKETG |
| 13 GVTAVAQKTN | 34 — | 61 — |
| 16 ATGFVKKDQL | 36 — | 64 LKFTKDVQGA |

The non-amyloid component (NAC) is located between ~61 and 95 and seemed to be relevant in the binding of α-Syn-Abs to α-Syn. This data was confirmed by SPR data that also showed that the α-Syn fragments containing the NAC region had a higher binding specificity to α-Syn as compared to fragments that lacked this region (data not shown).

To validate results obtained from the Dot Blot analysis, we selectively synthesized an overlapping peptide array through the NAC region of α-synuclein (residues 61-100) of hexamer peptides with a sliding window of 3 amino acids. A total of 11 peptide spots were generated to cover the complete NAC region of α-synuclein. These spots were numbered sequentially from 73-83. In addition to the overlapping peptides, we added a scrambled version, numbered 85-95 as well as a version with an amino acid randomly changed, numbered 87-107. The α-synuclein peptide array was probed with α-Syn-nAbs and spots on the array produced binding signals. The peptide sequences corresponding to positive signals are shown in Table 8.

TABLE 8

List of α-synuclein NAC region peptides that showed significant binding to α-Syn-nAbs in the peptide array membrane. The corresponding sequence with one aa change and the scrambled version were negative and therefore marked with -.

| Sequence | One aa change | scrambled |
|---|---|---|
| 77 VTAVAQ | 89 — | 101 — |
| 83 TGFVKK | 95 F>M TGMVKK | 107 KTKGFV |

2.5 α-Syn-Abs Inhibit the α-Syn Fibril Formation.

We investigated whether purified α-Syn-Abs had an effect on α-Syn fibril formation by using Thioflavin T (ThT), a fluorescent reagent that specifically binds to fibrillar structures. Incubation of highly concentrated α-Syn (4 mg/ml) alone resulted in a time-dependent increase in fluorescence as the α-Syn began to aggregate (FIG. 14*a*). Incubation of α-Syn with 2 μM affinity-purified α-Syn-Abs incubated for four days at 37° C. and 600 rpm caused a significant decrease in ThT fluorescence, suggesting that the affinity-purified autoantibody was able to reduce fibril formation of α-Syn (FIG. 14*b*). The antibody isolated from serum did not show the same capacity for inhibiting fibril formation as compared to the antibody isolated from IVIG. When α-Syn was incubated with the column flow-through, a decrease in fibril formation was observed. The resulting data was analysed by a t-test using the GraphPad Software (GraphPad Software Inc., San Diego, Calif.).

2.6 Affinity-Purified α-Syn Antibodies Block Cytotoxicity of Aggregated α-Syn

We examined the cytotoxicity of pre-aggregated α-Syn samples on the human neuroblastoma cell line SH-SY5Y using an MTT assay. We tested whether the affinity-purified α-Syn-Abs had an effect on α-Syn-mediated cytotoxicity. Cells were treated with α-Syn and pre-incubated for four days with or without α-Syn-Abs. As depicted in FIG. 15, there was a significant increase in cell viability when cells were treated with α-Syn in the presence of α-Syn-Abs. Incubation with an unspecific synthetic antibody did not produce the same effect. The resulting data were analyzed with one way analysis of variance (ANOVA) using the SigmaStat Software (Systat Software GmbH, Erkrath, Germany).

2.7. Amino Acid Sequence Determination of IgG1 Variable Domains of Heavy and Light Chains of Naturally Occurring Antibodies Directed Against α-Synuclein In order to obtain information on the amino acid sequence of the three complementarity determining regions (CDR) of each involved antibody chain as well as the relevant combination of the CDR1, CDR2, and CDR3 an RT-PCR/cDNA-sequencing approach using B-cell derived mRNA as template was performed.

Briefly, RNA was first isolated from B-cells enriched for anti-α-Syn, which were derived from blood donation buffy coats. Subsequently, cDNA was generated from the mRNA by oligo-dT priming. The cDNA was used as substrate for two types of PCR. The first PCR was specific for the variable domain of all human IgG1 heavy chains including a fragment of the adjoining constant domain. The second PCR was specific for the variable domain of human Kappa light chain plus a part of the neighboring sequences derived from the constant domain of the kappa light chain. These PCRs generate fragments of the variable domains of heavy and light chains from various B-cells thus demonstrating a mixture of information on these molecules from different cells. To be able to generate information on single HC/LC molecules, the PCR products were cloned into plasmids. Finally, colony-PCR products of the right size were sequenced and the nucleotide information translated into the required amino acid information. This information could be analyzed for its relationship to the expected IgG1 sequences as well as for statistical distribution of the number of sequences found within the samples.

The sequences determined for exemplary α-Syn specific light chains are shown in SEQ ID NOs.: 2, 148, 149, 150, and 151.

2.8. Statistical Evaluation

Statistical Evaluation for IgG1 $HC_v$ Amino Acid Sequences

Number of sequences analysed:

| | |
|---|---|
| Sequences in total: | 100 (100%) |
| IgM related sequences: | 11 (11%) |
| IgG1 related but truncated: | 9 (9%) |
| IgG1 related sequences: | 80 (80%) |

IgG1 $HC_v$ types defined due to sequence homologies:

| | |
|---|---|
| Type1: | 48 (60%) |
| Type2: | 13 (16%) |
| Type3: | 19 (24%) |

Homology between Type1/Type2/Type3 consensus sequences (without CDR regions):

| | |
|---|---|
| Type1/Type2: | 76% |
| Type2/Type3: | 64% |
| Type1/Type3: | 71% |

Number of CDR sequences detected within IgG1 $HC_v$:

| | | | | | |
|---|---|---|---|---|---|
| CDR1: | 13 | CDR2: | 14 | CDR3: | 31 |
| Type1: | 6 | Type1: | 8 | Type1: | 20 |
| Type2: | 2 | Type2: | 2 | Type2: | 5 |
| Type3: | 5 | Type3: | 4 | Type3: | 6 |

No CDR region found within one type of α-Syn specific IgG1 $HC_v$ was found in another type as well.

Number of CDR1/CDR2/CDR3 combinations detected:

| | | | | |
|---|---|---|---|---|
| Total: | 45 | | | |
| Type1: | 30 | within 48 clones => ratio | 0.63 | new combinations per clone |
| Type2: | 6 | within 13 clones => ratio | 0.46 | |
| Type3: | 9 | within 19 clones => ratio | 0.47 | |

The statistics presented here do not reflect the similarity by the detected amino acid sequences within the CDR groups. The combinations mentioned within the calculations above often differ by one single amino acid only.

Statistical Evaluation for Kappa $LC_v$ Amino Acid Sequences

Number of sequences analysed:

| | |
|---|---|
| Sequences in total: | 137 (100%) |
| Non κLCv related sequences: | 12 (9%) |
| κLCv related but truncated: | 0 (0%) |
| κLCv related sequences: | 125 (91%) |

κLCv types defined due to sequence homologies:

| | | |
|---|---|---|
| Type1: | 64 (51%) | |
| Type2: | 24 (19%) | |
| Type3: | 33 (27%) | |
| Not defined: | 4 (3%) | (not considered for further evaluation) |

Homology between Type1/Type2/Type3 consensus sequences (without CDR regions):

| | |
|---|---|
| Type1/Type2: | 76% |
| Type2/Type3: | 74% |
| Type1/Type3: | 68% |

Number of CDR sequences detected within κLCv:

| | | | | | |
|---|---|---|---|---|---|
| CDR1: | 11 | CDR2: | 9 | CDR3: | 25 |
| Type1: | 1 | Type1: | 1 | Type1: | 4 |
| Type2: | 3 | Type2: | 3 | Type2: | 8 |
| Type3: | 7 | Type3: | 5 | Type3: | 13 |

No CDR region found within one type of α-Syn specific κLCv was found in another type as well.

Number of CDR1/CDR2/CDR3 combinations detected:

| | | | | |
|---|---|---|---|---|
| Total: | 30 | | | |
| Type1: | 4 | within 64 clones => ratio | 0.06 | new combinations per clone |
| Type2: | 10 | within 24 clones => ratio | 0.42 | new combinations per clone |
| Type3: | 16 | within 33 clones => ratio | 0.48 | new combinations per clone |

The statistics presented here do not reflect the similarity by the detected amino acid sequences within the CDR groups. The combinations mentioned within the calculations above often differ by one single amino acid only.

3. Discussion

Neuropathologic and genetic studies as well as the development of transgenic animal models have provided evidence for the involvement of α-Synuclein (α-Syn) in the pathogenesis of Parkinson's disease (PD). It has become increasingly evident that the misfolded and aggregated species of α-Syn are known to be neurotoxic and subsequently lead to neurodegeneration. Thus, research has focused on finding new approaches to reducing abnormal accumulation of α-Syn.

In recent years, immunization has been shown to be effective in reducing neuronal accumulation of α-Syn aggregates. Masliah and colleagues also demonstrated that active immunization against human α-Syn reduced α-Syn aggregates in the brains of transgenic mice (Masliah et al., 2005). Papachroni and colleagues demonstrated for the first time the existence of autoantibodies (AAbs) against α-Syn that are positively correlated with the familial but not sporadic form of PD. In the study, they examined the presence of AAbs against α-Syn in the peripheral blood serum of PD patients and controls. They could detect such AAbs in 65% of all tested patients and they demonstrated that 90% of patients with familial PD tested positive for AAbs against α-Syn. Therefore, they hypothesized that these AAbs could be involved in the pathogenesis of α-Syn. (Papachroni et al., 2007).

Emadi and colleagues have isolated a human single-chain antibody fragment (scFv) against oligomeric α-Syn from a phage display antibody library (Emadi et al., 2007). They described binding only to oligomeric forms of α-Syn and inhibited both aggregation and toxicity of α-Syn in vitro. This approach is considered a significant advance toward a molecular therapy targeted against PD and other neurodegenerative conditions in which α-Syn aggregations represent a primary hallmark of disease.

In this study, we were able to isolate naturally occurring α-Syn antibodies from IVIG as well as from the serum of a healthy donor. Subsequent characterization by different assays including ELISA, Western blot analysis and surface plasmon resonance (SPR) analysis demonstrated that these α-Syn antibodies recognize several species of α-Syn. ELISA showed that antibodies purified from IVIG and from the serum of a single donor could both bind α-Syn. Western blot analysis demonstrated that the autoantibody was able to bind different species of α-Syn but not monomeric β- and γ-Synuclein. These results were confirmed using SPR analysis: the binding of the autoantibody was shown to be specific for monomeric α-Syn but not for monomeric β- or γ-Syn. Interestingly, oligomeric forms of all three synucleins were also recognized.

Our attempt to characterize the linear binding epitope of our α-Syn-Abs indicated that the non amyloidal component (NAC) region might be of importance. The NAC Region was originally identified as a component of Alzheimer's amyloid plaques. Deletions of this regions have been shown to be crucial for the aggregation of α-Syn in vitro (Ueda et al., 1993, Conway et al., 1998, Takeda et al., 1998) and through their toxicity to dopaminergic neurons in a Drosophila model (Periquet et al., 2007).

We were able to determine the cellular and subcellular localization of the binding partners of the α-Syn-Abs in the brains of PD patients as well as in the brains of transgenic mice by immunohistochemistry. The functionality of the affinity-purified α-Syn antibodies was tested using a thioflavin T assay and we were able to show that it can inhibit fibrillation of α-Syn. Also, a cell viability assay demonstrated that the affinity-purified α-Syn-Abs were able to increase cell viability and reduce α-Syn-induced cytotoxicity. These results are consistent with the effects of the antibodies against oligomeric forms of α-Syn as published in Emadi et al., 2007.

Taken together, these data suggest that the isolated α-Syn antibodies could have a therapeutic application in controlling the aggregation of α-Synuclein and consequently in the progression of PD.

REFERENCES

1. Conway K A, Harper J D, Lansbury P T (Accelerated in vitro fibril formation by a mutant alpha-synuclein linked to early-onset Parkinson disease. Nature medicine 4:1318-1320. 1998).
2. Dodel R, Hampel H, Depboylu C, Lin S, Gao F, Schock S, Jackel S, Wei X, Buerger K, Hoft C, Hemmer B, Moller H J, Farlow M, Oertel W H, Sommer N, Du Y (Human antibodies against amyloid beta peptide: a potential treatment for Alzheimer's disease. Annals of neurology 52:253-256. 2002).
3. Du Y, Wei X, Dodel R, Sommer N, Hampel H, Gao F, Ma Z, Zhao L, Oertel W H, Farlow M (Human anti-beta-amyloid antibodies block beta-amyloid fibril formation and prevent beta-amyloid-induced neurotoxicity. Brain 126: 1935-1939. 2003).
4. Emadi S, Barkhordarian H, Wang M S, Schulz P, Sierks M R (Isolation of a human single chain antibody fragment against oligomeric alpha-synuclein that inhibits aggregation and prevents alpha-synuclein-induced toxicity. Journal of molecular biology 368:1132-1144. 2007).

5. Eriksen J L, Dawson T M, Dickson D W, Petrucelli L (Caught in the act: alpha-synuclein is the culprit in Parkinson's disease. Neuron 40:453-456. 2003).
6. Giasson B I, Murray I V, Trojanowski J Q, Lee V M (A hydrophobic stretch of 12 amino acid residues in the middle of alpha-synuclein is essential for filament assembly. The Journal of biological chemistry 276:2380-2386. 2001).
7. Hashimoto M, Masliah E (Alpha-synuclein in Lewy body disease and Alzheimer's disease. Brain pathology (Zurich, Switzerland) 9:707-720. 1999).
8. Herrera F E, Chesi A, Paleologou K E, Schmid A, Munoz A, Vendruscolo M, Gustincich S, Lashuel H A, Carloni P (Inhibition of alpha-synuclein fibrillization by dopamine is mediated by interactions with five C-terminal residues and with E83 in the NAC region. PLoS ONE 3:e3394. 2008).
9. Iwai A (Properties of NACP/alpha-synuclein and its role in Alzheimer's disease. Biochimica et biophysica acta 1502: 95-109. 2000).
10. Kahle P J, Neumann M, Ozmen L, Muller V, Odoy S, Okamoto N, Jacobsen H, Iwatsubo T, Trojanowski J C S, Takahashi H, Wakabayashi K, Bogdanovic N, Riederer P, Kretzschmar H A, Haass C (Selective insolubility of alpha-synuclein in human Lewy body diseases is recapitulated in a transgenic mouse model. The American journal of pathology 159:2215-2225. 2001).
11. Kayed R, Head E, Thompson J L, McIntire T M, Milton S C, Cotman C W, Glabe C G (Common structure of soluble amyloid oligomers implies common mechanism of pathogenesis. Science (New York, N.Y. 300:486-489. 2003).
12. Kim Y S, Lee D, Lee E K, Sung J Y, Chung K C, Kim J, Paik S R (Multiple ligand interaction of alpha-synuclein produced various forms of protein aggregates in the presence of Abeta25-35, copper, and eosin. Brain research 908:93-98. 2001).
13. Masliah E, Rockenstein E, Adame A, Alford M, Crews L, Hashimoto M, Seubert P, Lee M, Goldstein J, Chilcote T, Games D, Schenk D (Effects of alpha-synuclein immunization in a mouse model of Parkinson's disease. Neuron 46:857-868. 2005).
14. Masliah E, Rockenstein E, Veinbergs I, Mallory M, Hashimoto M, Takeda A, Sagara Y, Sisk A, Mucke L (Dopaminergic loss and inclusion body formation in alpha-synuclein mice: implications for neurodegenerative disorders. Science (New York, N.Y. 287:1265-1269. 2000).
15. Murphy R C, Messer A (A single-chain Fv intrabody provides functional protection against the effects of mutant protein in an organotypic slice culture model of Huntington's disease. Molecular Brain Research 121:141-145. 2004).
16. Papachroni K K, Ninkina N, Papapanagiotou A, Hadjigeorgiou G M, Xiromerisiou G, Papadimitriou A, Kalofoutis A, Buchman V L (Autoantibodies to alpha-synuclein in inherited Parkinson's disease. Journal of neurochemistry 101:749-756. 2007).
17. Park S M, Jung H Y, Kim T D, Park J H, Yang C H, Kim J (Distinct roles of the N-terminal-binding domain and the C-terminal-solubilizing domain of alpha-synuclein, a molecular chaperone. The Journal of biological chemistry 277:28512-28520. 2002).
18. Periquet M, Fulga T, Myllykangas L, Schlossmacher M G, Feany M B (Aggregated alpha-synuclein mediates dopaminergic neurotoxicity in vivo. J Neurosci 27:3338-3346. 2007).
19. Polymeropoulos M H, Lavedan C, Leroy E, Ide S E, Dehejia A, Dutra A, Pike B, Root H, Rubenstein J, Boyer R, Stenroos E S, Chandrasekharappa S, Athanassiadou A, Papapetropoulos T, Johnson W G, Lazzarini A M, Duvoisin R C, Di Iorio G, Golbe L I, Nussbaum R L (Mutation in the alpha-synuclein gene identified in families with Parkinson's disease. Science (New York, N.Y. 276:2045-2047. 1997).
20. Singleton A B, Farrer M, Johnson J, Singleton A, Hague S, Kachergus J, Hulihan M, Peuralinna T, Dutra A, Nussbaum R, Lincoln S, Crawley A, Hanson M, Maraganore D, Adler C, Cookson M R, Muenter M, Baptista M, Miller D, Blancato J, Hardy J, Gwinn-Hardy K (alpha-Synuclein locus triplication causes Parkinson's disease. Science (New York, N.Y. 302:841. 2003).
21. Spillantini M G, Schmidt M L, Lee V M, Trojanowski J Q, Jakes R, Goedert M (Alpha-synuclein in Lewy bodies. Nature 388:839-840. 1997).
22. Takeda A, Hashimoto M, Mallory M, Sundsumo M, Hansen L, Sisk A, Masliah E (Abnormal distribution of the non-Abeta component of Alzheimer's disease amyloid precursor/alpha-synuclein in Lewy body disease as revealed by proteinase K and formic acid pretreatment. Laboratory investigation; a journal of technical methods and pathology 78:1169-1177. 1998).
23. Takenouchi T, Hashimoto M, Hsu L J, Mackowski B, Rockenstein E, Mallory M, Masliah E (Reduced neuritic outgrowth and cell adhesion in neuronal cells transfected with human alpha-synuclein. Molecular and cellular neurosciences 17:141-150. 2001).
24. Ueda K, Fukushima H, Masliah E, Xia Y, Iwai A, Yoshimoto M, Otero D A, Kondo J, Ihara Y, Saitoh T (Molecular cloning of cDNA encoding an unrecognized component of amyloid in Alzheimer disease. Proceedings of the National Academy of Sciences of the United States of America 90:11282-11286. 1993).
25. Wakabayashi K, Hayashi S, Kakita A, Yamada M, Toyoshima Y, Yoshimoto M, Takahashi H (Accumulation of alpha-synuclein/NACP is a cytopathological feature common to Lewy body disease and multiple system atrophy. Acta neuropathologica 96:445-452. 1998).
26. Zarranz J J, Alegre J, Gomez-Esteban J C, Lezcano E, Ros R, Ampuero I, Vidal L, Hoenicka J, Rodriguez O, Atares B, Llorens V, Gomez Tortosa E, del Ser T, Munoz D G, de Yebenes J G (The new mutation, E46K, of alpha-synuclein causes Parkinson and Lewy body dementia. Annals of neurology 55:164-173. 2004).
27. Zhou W, Huribert M S, Schaack J, Prasad K N, Freed C R (Overexpression of human alpha-synuclein causes dopamine neuron death in rat primary culture and immortalized mesencephalon-derived cells. Brain research 866:33-43. 2000).

The invention claimed is:

1. An isolated human antibody which is directed against an epitope between amino acids 60-100 of human α Synuclein (α-Syn), or a fragment of said antibody, which comprises a heavy chain comprising complementarity determining regions CDR1, CDR2, and CDR3, wherein CDR1 is selected from the sequences shown in SEQ ID NOs.: 76-80, CDR2 is selected from the sequences shown in SEQ ID NOs.: 82-85, and CDR3 is selected from the sequences shown in SEQ ID NOs.: 86-91.

2. An isolated human antibody which is directed against an epitope between amino acids 60-100 of human α Synuclein (α-Syn), or a fragment of said antibody, which comprises a light chain comprising complementarity determining regions CDR1, CDR2, and CDR3, wherein CDR1 is selected from the sequences shown in SEQ ID NOs.: 116-122, CDR2 is selected from the sequences shown in SEQ ID NOs.: 123-127, and CDR3 is selected from the sequences shown in SEQ ID NOs.: 128-144.

3. An isolated human antibody which is directed against an epitope between amino acids 60-100 of human α Synuclein (α-Syn), or a fragment of said antibody, which comprises a heavy chain comprising framework regions consisting of a consensus sequence as shown in SEQ ID NOs.: 11-14 or variants thereof, further comprising complementarity determining regions CDR1, CDR2, and CDR3, wherein CDR1 is selected from the sequences shown in SEQ ID NOs.: 76-80, CDR2 is selected from the sequences shown in SEQ ID NOs.: 82-85, and CDR3 is selected from the sequences shown in SEQ ID NOs.: 86-91.

4. An isolated human antibody which is directed against an epitope between amino acids 60-100 of human α Synuclein (α-Syn), or a fragment of said antibody, which comprises a light chain comprising framework regions consisting of a consensus sequence as shown in SEQ ID NOs.: 23-26 or variants thereof, further comprising complementarity determining regions CDR1, CDR2, and CDR3, wherein CDR1 is selected from the sequences shown in SEQ ID NOs.: 116-122, CDR2 is selected from the sequences shown in SEQ ID NOs.: 123-127, and CDR3 is selected from the sequences shown in SEQ ID NOs.: 128-144.

* * * * *